US007173125B2

(12) United States Patent
Schwartz et al.

(10) Patent No.: US 7,173,125 B2
(45) Date of Patent: Feb. 6, 2007

(54) TRIPHOSPHATE OLIGONUCLEOTIDE MODIFICATION REAGENTS AND USES THEREOF

(76) Inventors: David A. Schwartz, 1544 Valleda La., Encinitas, CA (US) 92024; Richard I. Hogrefe, 6045 Dirac St., San Diego, CA (US) 92121

( * ) Notice: Subject to any disclaimer, the term of this patent is extended or adjusted under 35 U.S.C. 154(b) by 546 days.

(21) Appl. No.: 10/720,840

(22) Filed: Nov. 24, 2003

(65) Prior Publication Data

US 2004/0214199 A1   Oct. 28, 2004

Related U.S. Application Data

(62) Division of application No. 09/630,627, filed on Aug. 1, 2000, now Pat. No. 6,686,461.

(51) Int. Cl.
C07H 19/04    (2006.01)
C07H 19/20    (2006.01)
A61K 31/70    (2006.01)
A01N 83/04    (2006.01)

(52) U.S. Cl. ............... 536/26.26; 536/22.1; 536/25.3; 536/25.32

(58) Field of Classification Search ............ 536/26.26, 536/22.1, 25.3, 25.32
See application file for complete search history.

(56) References Cited

U.S. PATENT DOCUMENTS

| | | | |
|---|---|---|---|
| 3,939,123 A | 2/1976 | Matthews et al. | 260/77.5 |
| 4,006,117 A | 2/1977 | Merrifield | 260/45.9 |
| 4,162,355 A | 7/1979 | Tsibris | 526/293 |
| 4,171,412 A | 10/1979 | Coupek et al. | 525/329 |
| 4,175,183 A | 11/1979 | Ayers | 536/57 |
| 4,177,038 A | 12/1979 | Biebricher et al. | 8/192 |
| 4,178,439 A | 12/1979 | Ayers et al. | 536/59 |
| 4,180,524 A | 12/1979 | Reusser et al. | 585/644 |
| 4,241,537 A | 12/1980 | Wood | 47/77 |
| 4,337,063 A | 6/1982 | Mihara et al. | 23/230 |
| 4,404,289 A | 9/1983 | Masuda et al. | 436/538 |
| 4,405,711 A | 9/1983 | Masuda et al. | 435/4 |
| 4,439,585 A | 3/1984 | Gould et al. | 525/127 |
| 4,485,227 A | 11/1984 | Fox | 528/61 |
| 4,507,230 A | 3/1985 | Tam et al. | 260/112.5 |
| 4,569,981 A | 2/1986 | Wenzel et al. | 528/67 |
| 4,683,202 A | 7/1987 | Mullis | 435/91 |
| 4,707,440 A | 11/1987 | Stavrianopoulos | 435/6 |
| 4,833,251 A | 5/1989 | Musso et al. | 548/303 |
| 4,874,813 A | 10/1989 | O'Shannessy | 525/54.1 |
| 4,889,798 A | 12/1989 | Rabbani | 435/6 |
| 4,927,879 A | 5/1990 | Pidgeon | 525/54.1 |
| 4,931,498 A | 6/1990 | Pidgeon | 525/54.1 |
| 5,092,992 A | 3/1992 | Crane et al. | 210/198.2 |
| 5,130,446 A | 7/1992 | Musso et al. | 549/223 |
| 5,151,507 A | 9/1992 | Hobbs, Jr. et al. | 536/23 |
| 5,206,370 A | 4/1993 | Schwartz et al. | 546/281 |
| 5,210,203 A | 5/1993 | Musso et al. | 548/130 |
| 5,237,016 A | 8/1993 | Ghosh et al. | 525/329.4 |
| 5,242,756 A | 9/1993 | Hensel et al. | 428/480 |
| 5,242,796 A | 9/1993 | Prober et al. | 435/6 |
| 5,328,603 A | 7/1994 | Velander et al. | 210/198.2 |
| 5,334,640 A | 8/1994 | Desai et al. | 524/56 |
| 5,389,449 A | 2/1995 | Afeyan et al. | 428/523 |
| 5,403,750 A | 4/1995 | Braatz et al. | 436/531 |
| 5,420,285 A | 5/1995 | Schwartz et al. | 546/281 |
| 5,432,018 A | 7/1995 | Dower et al. | 435/5 |
| 5,474,895 A | 12/1995 | Ishii et al. | 435/6 |
| 5,478,893 A | 12/1995 | Ghosh et al. | 525/329.4 |
| 5,486,616 A | 1/1996 | Waggoner et al. | 548/217 |
| 5,521,290 A | 5/1996 | Sivam et al. | 530/391.5 |
| 5,547,835 A | 8/1996 | Koster | 435/6 |
| 5,547,839 A | 8/1996 | Dower et al. | 435/6 |
| 5,556,752 A | 9/1996 | Lockhart et al. | 435/6 |
| 5,569,587 A | 10/1996 | Waggoner et al. | 435/6 |
| 5,569,766 A | 10/1996 | Waggoner et al. | 548/150 |
| 5,627,027 A | 5/1997 | Waggoner | 435/6 |
| 5,663,242 A | 9/1997 | Ghosh et al. | 525/329.4 |
| 5,679,778 A | 10/1997 | Abrams et al. | 530/391.5 |
| 5,726,329 A | 3/1998 | Jones et al. | 552/105 |
| 5,741,462 A | 4/1998 | Nova et al. | 422/68.1 |

(Continued)

FOREIGN PATENT DOCUMENTS

EP    0361768 A2    9/1989

(Continued)

OTHER PUBLICATIONS

Abrams et al., Technetium-99m-Human Polyclonal IgG Radiolabeled via the Hydrazino Nicotinamide Derivative for Imaging Focal Sites of Infection in Rats, *The Journal of Nuclear Medicine* 31(12): 2022-8 (1990).

(Continued)

*Primary Examiner*—Patrick Lewis
(74) *Attorney, Agent, or Firm*—David B. Waller & Associates

(57) ABSTRACT

Hydrazino, oxyamino and carbonyl-based monomers and methods for incorporation into oligonucleotides during enzymatic synthesis are provided. Modified oligonucleotides are provided that incorporate the monomers provided herein. Immobilized oligonucleotides and oligonucleotide conjugates that contain covalent hydrazone or oxime linkages are provided. Methods for preparation of surface bound oligonucleotides are provided. Methods for the preparation of oligonucleotide conjugates are also provided.

10 Claims, 9 Drawing Sheets

U.S. PATENT DOCUMENTS

| | | | |
|---|---|---|---|
| 5,744,305 A | 4/1998 | Fodor et al. | 435/6 |
| 5,751,629 A | 5/1998 | Nova et al. | 365/151 |
| 5,753,520 A | 5/1998 | Schwartz et al. | 436/542 |
| 5,789,576 A | 8/1998 | Daily et al. | 536/25.6 |
| 5,792,615 A | 8/1998 | Arnold et al. | 435/6 |
| 5,824,473 A | 10/1998 | Meade et al. | 435/6 |
| 5,837,856 A | 11/1998 | Arnold, Jr. et al. | 536/24.5 |
| 5,837,860 A | 11/1998 | Anderson et al. | 536/25.3 |
| 5,854,410 A | 12/1998 | Arnold, Jr. et al. | 536/23.1 |
| 5,856,571 A | 1/1999 | Berninger et al. | 564/37 |
| 5,874,214 A | 2/1999 | Nova et al. | 435/6 |
| 5,874,552 A | 2/1999 | Jones et al. | 536/22.1 |
| 5,876,938 A | 3/1999 | Stolowitz et al. | 435/6 |
| 5,877,220 A | 3/1999 | Schwartz et al. | 514/626 |
| 5,880,270 A | 3/1999 | Berninger et al. | 530/391.1 |
| 5,925,562 A | 7/1999 | Nova et al. | 435/287.1 |
| 5,952,172 A | 9/1999 | Meade et al. | 435/6 |
| 5,955,597 A | 9/1999 | Arnold, Jr. et al. | 536/24.3 |
| 5,958,901 A | 9/1999 | Dwyet et al. | 514/75 |
| 5,961,923 A | 10/1999 | Nova et al. | 422/68.1 |
| 5,972,639 A | 10/1999 | Parandoosh | 435/29 |
| 6,001,826 A | 12/1999 | Murrer et al. | 514/183 |
| 6,017,496 A | 1/2000 | Nova et al. | 422/68.1 |
| 6,020,526 A | 2/2000 | Schwartz et al. | 564/153 |
| 6,025,129 A | 2/2000 | Nova et al. | 435/6 |
| 6,028,188 A | 2/2000 | Arnold, Jr. et al. | 536/25.3 |
| 6,034,135 A | 3/2000 | Schwartz et al. | 514/616 |
| 6,066,448 A | 5/2000 | Wohlstacter et al. | 435/6 |
| 6,071,699 A | 6/2000 | Meade et al. | 435/6 |
| 6,074,823 A | 6/2000 | Koster | 435/6 |
| 6,087,186 A | 7/2000 | Cargill et al. | 436/518 |
| 6,217,845 B1 | 4/2001 | Schwartz et al. | 424/1.69 |

FOREIGN PATENT DOCUMENTS

| | | |
|---|---|---|
| EP | 0384769 A2 | 2/1990 |
| EP | 0384769 B1 | 2/1990 |
| EP | 0772135 A1 | 6/1996 |
| WO | 9815825 | 4/1998 |
| WO | 9831732 | 7/1998 |
| WO | 9835978 | 8/1998 |
| WO | 9965993 | 12/1999 |
| WO | 0004382 | 1/2000 |
| WO | 0004389 | 1/2000 |
| WO | 0004390 | 1/2000 |
| WO | 0008042 A1 | 2/2000 |
| WO | 0040590 A2 | 7/2000 |
| WO | 0040590 A3 | 7/2000 |
| WO | 0109385 A2 | 2/2001 |

OTHER PUBLICATIONS

Bischoff et al., Introduction of 5'-Terminal Functional Groups into Synthetic Oligonucleotides for Selective Immobilization, *Anal. Biochem.* 164: 336-44 (1987).

Browne, D.W. and G.M. Dyson, 47. The Inhibitory Effect of Substituents in Chemical Reactions. Part III. The Reactivity of the isoThiocyano-group in Substituted Arylthiocarbimides, *J. Chem. Soc.* pp. 178-179 (1924).

Chang et al., Early Results in the International Design of New Bifunctional Chelators, *6th Conference on Radioimmunodetection and Radioimmunotherapy of Cancer-Supplement to Cancer 80:* 2347-53 (1997).

Frutos et al., Reversible Protection and Reactive Patterning of Amine- and Hydroxyl-Terminated Self-Assembled Monolayers on Gold Surfaces for the Fabrication of Biopolymer Arrays, *Langmuir* 16: 2192-7 (2000).

Ghosh et al., Covalent attachment of oligonucleotides to solid supports, *Nucl. Acids. Res.* 15(3):5353-72 (1987).

Ghosh et al., Synthesis of 5'-Oligonucleotide Hydrazide Derivatives and Their Use in Preparation of Enzyme-Nucleic Acid Hybridization Probes, *Anal. Biochem.* 178: 43-51 (1989).

Hakala et al., Detection of Oligonucleotide Hybridization on a Single Microparticle by Time-Resolved Fluorometry: Hybridization Assays on Polymer Particles obtained by Direct Solid Phase Assembly of the Oligonucleotide Probes, *Bioconjugate Chem.* 8: 378-84 (1997).

Hakala et al., Detection of Oligonucleotide Hybridization on a Single Microparticle by Time-Resolved Fluorometry: Quantiation and Optimization of a Sandwich Type Assay, *Bioconjugate Chem.* 9: 316-21 (1998).

Hogrefe, R.I., An Antisense Oligonucleotide Primer, *Antisense & Nucleic Acid Drug Development* 9: 351-7 (1999).

Hogrefe et al., An Improved Method for the Synthesis and Deprotection of Methylphosphonate Oligonucleotides, *Chapter 7 in Methods in Molecular Biology* vol. 20: *Protocols for Oligonucleotides and Analogs* Agrawal, S. (Ed.) Humana Press Inc., Totowa, NJ. pp. 143-164 (1993).

Hnatowich et al., Comparative Properties of a Technetium-99m-Labeled Single Stranded Natural DNA and a Phosphorothioate Derivative *in Vitro* and in Mice, *The Journal of Pharmacology and Experimental Therapeutics* 276: 326-34 (1996).

Hnatowich, D.J., Pharmacokinetics of 99m Tc-labeled oligonucleotides, *Q J Nucl. Med.* 40: 202-8 (1996).

Hnatowich et al., Technetium-99m Labeling of DNA Oligonucleotides, *The Journal of Nuclear Medicine* 36(12): 2306-14 (1995).

Kaneko et al., New Hydraone Derivatives of Adriamycin and Their Immunoconjugates—a Correlation between Acid Stability and Cytotoxicity, *Bioconjugate Chem.* 2(3): 133-41 (1991).

Kremsky et al., Immobilization of DNA via oligonucleotides containing an aldehyde or carboxylic acid group at the 5' terminus, *Nucl. Acids. Res.* 15(7): 2891-909 (1987).

Pidgeon et al., Solid Phase Membrane Mimetics: Immobilized Artifical Membranes, *Enzyme Microb. Technol.* 12: 149-50 (1990).

Reynolds et al., Antisense oligonucleotides containing an internal non-nucleotide-based linker promote site-specific cleavage of RNA, *Nucl. Acids. Res.* 24(4): 760-5 (1996).

Reynolds et al., A Non-Nucleotide-Based Linking Method for the Preparation of Psoralen-Derivatized Methylphosphonate Oligonucleotides, *Bioconjugate Chem.* 3: 366-74 (1992).

Reynolds et al., Synthesis and thermodynamics of oligonucleotides containing chirally pure Rp methylphosphonate linkages, *Nucl. Acids. Res.* 24(22): 4584-91 (1996).

Rogers et al., Immobilization of Oligonucleotides onto a Glass Support via Disulfide Bonds: A Method for Preparation of DNA Microarrays, *Anal. Biochem.* 266: 23-30 (1999).

Rusckowski et al., Effect of Endogenous Biotin on the Applications of Streptavidin and Biotin in Mice, *Nuclear Medicine & Biology* 24:263-8 (1997).

Rusckowski et al., Imaging Osteomyelitis with Streptavidin and Indium-111-Labeled Biotin, *J. Nuclear Medicine* 37: 1655-62 (1996).

Rusckowski et al., Pretargeting Using Peptide Nucleic Acid, *6th Conference on Radioimmunodetection and radioimmunotherapy of Cancer -Supplement to Cancer 80*: 2699-705 (1997).

Salo et al., Aminooxy Functionalized Oligonucleotides: Preparation, On-Support Derivatization, and Postsynthetic Attachment to Polymer Support, *Bioconjugate Chem.* 10: 815-23 (1999).

Salo et al., Disulfide-Tethered Solid Supports for Synthesis of Photoluminescent Oligonucleotide Conjugates: Hydrolytic Stability and Labeling on the Support, *Bioconjugate Chem.* 9: 365-71 (1998).

Schwartz et al., Preparation of Hydrazino-Modified Proteins and Their Use for the Synthesis of 99m Tc-Protein Conjugates, Bioconjugate Chem. 2:333-6 (1991).

Timofeev et al., Regioselective immobilization of short oligonucleotides to acrylic copolymer gels, *Nucl. Acids. Res.* 24(16): 3142-8 (1996).

Trevisiol et al., The Oxyamino-Aldehyde Coupling Reaction: An Efficient Method for the Derivatization of Oligonucleotides, *Tetrahedron Letters* 38(50): 8687-90 (1997).

Trevisiol et al., Synthesis of Nucleoside Triphosphate that Contain an Aminooxy Function for "Post-Ampification Labeling", *Eur. J. Org. Chem.* Jan. 2000(N1): 211-7.

Watkins, T.I., 585. Trypanocides of the Phenanthridine Series. Part I. The Effect of Changing the Quaternary Grouping in Dimidium Bromide, *J. Chem. Soc.* pp. 3059-3064 (1952).

"IUPAC-IUB Commission on Biochemical Nomenclature, Abbreviated Nomenclature of Synthetic Polypeptides (Polymerized Amino Acids), Revised Recommendations (1971)," *Biochem.* 11(5): 942-4 (1972).

Adleman et al. "Molecular Computation of Solutions to Combinatorial Problems," *Science* 266: 1021-4 (1994).

Agrawal, S. "Importance of nucleotide sequence and chemical modifications of antisense oligonucleotides," *Biochim. Biophys. Acta.* 1489: 53-68 (1999).

Berg et al. "Polystyrene-Grafted Polyethylene: Design of Film and felt Matrices for Solid-Phase Peptide Synthesis," *Innovation Perspect. Solid Phase Synth. Collect. Pap.*, Int. Symp., 1st, Epton R. (Ed.) pp. 453-459 (1989).

Berg et al. "Long-Chain Polystyrene-Grafted Polyethylene Film Matrix: A New Support for Solid-Phase Peptide Synthesis," *J. Am. Chem. Soc.* 111: 8024-6 (1989).

Berg et al. "Peptide Synthesis on Polystyrene-Grafted Polyethylene Sheets," *Pept. Proc. Eur. Pept. Symp.*, 20th, Jung, G. et al. (Eds.) pp. 196-198 (1989).

Bielinska et al. "Application of membrane-based dendrimer/DNA complexes for solid phase transfection in vitro and in vivo," *J. Biomaterials* 21: 877-887 (2000).

Blomqvist et al. "Rapid Detection of Human Rhinoviruses in Nasopharyngeal Aspirates by a Microwell Reserve Transcription-PCR-Hybridization Assay," *J. Clin. Microbiol.* 37: 2813-6 (1999).

Brown, M.P. and Royer, C. "Fluorescence spectroscopy as a tool to investigate protein," *Curr. Opin. Biotechnol.* 8: 45-9 (1997).

Carlsson, B. and Haggblad, J. "Quantitative Determination of DNA-Binding Parameters for the Human Estrogen Receptor in a Solid-Phase Nonseparation Assay," *Anal. Biochem.* 232: 172-9 (1995).

Chen et al. "Stable-Isotope-Assisted MALDI-TOF Mass Spectrometry for Accurate Determination of Nucleotide Compositions of PCR Products," 71: 3118-25 (1999).

Compagno et al. "Antisense Oligonucleotides Containing Modified Bases Inhibit *in Vitro* Translation of *Leishmania amazonensis* mRNAs by Invading the Mini-exon Hairpin," *J. Biol. Chem.* 274: 8191-8 (1999).

Cristiano, R. J. and Roth, J.A. "Epidermal growth factor mediated DNA delivery into lung cancer cells via the epidermal growth factor receptor," *Cancer Gene Therapy* 3: 4-10 (1996).

Crooke, S.T. "Molecular mechanisms of action of antisense drugs," *Biochim. Biophys. Acta.* 1489: 31-44 (1999).

De Benedetti et al. "DNA chips: the future of biomarkers," *Int. J. Biol. Markers* 15(1): 1-9 (2000).

Earnshaw et al. "Investigation of the Proposed Interdomain Ribose Zipper in Hairpin Ribozyme Cleavage Using 2'-Modified Nucleosides," *Biochemistry* 39: 6410-21 (2000).

Feinberg et al. "A Technique for Radiolabeling DNA Restriction Endonuclease Fragments to High Specific Activity," *Anal. Biochem.* 132: 6-13 (1983).

Filippov et al. "Solid-Phase Ligation of Synthetic DNA Fragments," *Bioorg Khim.* 16: 1045-51 (1990).

Flanagan et al. "A cytosine analog that confers enhanced potency to antisense oligonucleotides," *Proc. Natl. Acad. Sci. USA* 96: 3513-8 (1999).

Frutos et al. "Demonstration of a word design strategy for DNA computing on surfaces," *Nucl. Acids Res.* 25: 4787-57 (1997).

Frutos et al. "Enzymatic Ligation Reactions of DNA 'Words' on Surfaces for DNA Computing," *J. Am. Chem. Soc.* 120(40): 10277-82 (1998).

Fujita, K. and Silver, J. "Surprising Lability of Biotin-Streptavidin Bond During Transcription of Biotinylated DNA Bound to Paramagnetic Streptavidin Beads," *Biotechniques* 14(4): 608-17 (1993).

Gottschalk et al. "Efficient gene delivery and expression in mammalian cellsusing DNA coupled with perfringolysin O," *Gene Therapy* 2: 498-503 (1995).

Greene, T.W. and Wuts, P.G.M. (Eds.) *Protective Groups in Organic Synthesis* 3rd ed. (J. Wiley & Sons, Inc.) (1999).

Gryaznov, S.M. "Oligonucleotide N3' -> P5' phosphoramidates as potential therapeutic agents," *Biochim. Biophys. Acta* 1489: 131-40 (1999).

Hermanson et al. *Immobilized Affinity Ligand Techniques* (Academic Press, Inc., San Diego) 1992.

Hoganson et al. "Targeted Delivery of DNA Encoding Cytotoxic Proteins through High-Affinity Fibroblast Growth Factor Receptors," *Human Gene Therapy* 9: 2565-75 (1998).

Hostomsky et al. "Solid-phase assembly of DNA duplexes from synthetic oligonucleotides," *Nucl. Acid. Symp. Ser.* 18: 241-244 (1987).

Hultman et al. "Solid-phase cloning to create sublibraries suitable for DNA sequencing," *J. Biotechnol.* 35: 229-38 (1994).

Kari, L. "DNA Computing: Arrival of Biological Mathematics," *Mathematical Intelligencer* 19: 9-22 (1997).

Kent, S.B.H. and Merrifield, R.B. Preparation and Properties of *tert*-Butyloxycarbonylaminoacyl-4-(oxymethyl)phenylacetamidomethyl-(Kel F-g-styrene) Resin, an Insoluble, Noncrosslinked Support for Solid Phase Peptide Synthesis, *Isr. J. Chem.* 17: 243-7 (1978).

Kozwich et al. "Development of a Novel, Rapid, Integrated *Cryptosporidium parvum* Detection Assay," *Appl. Environ. Microbiol.* 66(6): 2711-7 (2000).

Kumar, Abhay et al. "Nonradioactive Labeling of Synthetic Oligonucleotide Probes with Terminal Deoxynucleotidyl Transferase," *Anal. Biochem.* 169: 376-82 (1988).

Lannutti et al. "Probing the Protein—DNA Contacts of a Yeast RNA Polymerase III Transcription Complex in a Crude Extract: Solid Phase Synthesis of DNA Photoaffinity Probes Containing a Novel Photoreactive Deoxycytidine Analog," *Biochemistry* 35: 9821-31 (1996).

Lee et al. "Direct Measurement of the Forces Between Complementary Strands of DNA," *Science* 266: 771-3 (1994).

Lees et al. "Activation of soluble polysaccharides with 1-cyano-4-dimethylaminopyridinium tetrafluoroborate for use in protein-polysaccharide conjugate vaccines and immunological reagents," *Vaccine* 14: 190-8 (1996).

Liu et al. "DNA computing on surfaces," *Nature* 403: 175-9 (2000).

Liu et al. "Progress toward demonstration of a surface based DNA computation: a one word approach to solve a model satisfiability problem," *BioSystems* 52: 25-33 (1999).

Liu et al. "DNA Computing on Surfaces: Encoding Information at the Single Base Level," *J. Comp. Biol.* 5: 269-278 (1998).

Lu et al. "Antisense DNA Delivery In Vivo: Liver Targeting by Receptor-Mediated Uptake," *J. Nucl. Med.* 35: 269-75 (1994).

Maeji et al. "Grafted supports used with the multipin method of peptide synthesis," *Reactive Polymers* 22: 203-12 (1994).

Marble et al. "RNA Transcription from Immobilized DNA Templates," *Biotechnol. Prog.* 11: 393-6 (1995).

Merrifeld, R.B. "Solid-Phase Peptide Synthesis. III. An Improved Synthesis of Bradykinin," *Biochemistry* 3: 1385-90 (1964).

Mitchell et al. "Preparation of Aminomethyl-Polystyrene Resin by Direct Amidomethylation," *Tetrahedron Lett.* 42: 3795-8 (1976).

Mitchell, A.R., Kent S.B.H. et al. "A New Synthetic Route to *tert*-Butyloxycarbonylaminoacyl-4-(oxymethyl)phenylacetamidomethl-resin, an Improved Support for Solid-Phase Synthesis," *J. Org. Chem.* 43: 2845-52 (1978).

Morishita, R. "Oligonucleotide-based therapy as a potential new pharmacotherapy," *Folia Pharmacol. Jpn. (Nippon Yakurigaku Zasshi)* 115: 123-30 (2000).

Muddiman et al. "Length and Base Composition of PCR-Amplifiedd Nucleic Acids Using Mass Measurements from Electrospray Ionization Mass Spectrometry," *Anal. Chem.* 69(8): 1543-1549 (1997).

Mustajoki et al. "Steady-State Transcript Levels of the Porphobilinogen Deaminase Gene in Patients with Acute Intermittent Porphyria," *Genome Res.* 7: 1054-60 (1997).

Niemeyer et al. "Oligonucleotide-directed self-assembly of proteins: semisynthetic DNA—streptavidin hybrid molecules as connectors for the generation of macroscopic arrays and the construction of supramolecular bioconjugates," *Nucl. Acids Res.* 22(25): 5530-9 (1994).

Perales et al. "An evaluation of receptor-mediated gene transfer using synthetic DNA-ligand complexes," *Eur. J. Biochem. 226*: 255-66 (1994).

Pinkel et al. "Cytogenetic analysis using quantitative, high-sensitivity, fluorescence hybridization," *Proc. Natl. Acad. Sci. USA 83*: 2934-8 (1986).

Powers et al. "Protein Purification by Affinity Binding to Unilamellar Vesicles," *Biotechnol. Bioorg. 33*: 173-82 (1989).

Reed, M.A. and Tror, J.M. "Computing with Molecules," *Scientific American* (Jun. 2000) pp. 86-93.

Rigby et al. "Labeling Deoxyribonucleic Acid to High Specific Activity *in Vitro* by Nick Translation with DNA Polymerase I," *J. Mol. Biol. 113*: 237-51 (1977).

Roth, A. and Messer, W. "The DNA binding domain of the initiator protein," *EMBO J. 14*: 2106-11 (1995).

Salles et al. "DNA damage excision repair in microplate wells with chemiluminescence detection: Development and perspectives," *Biochimie 81*: 53-8 (1999).

Shafer, D.E., Lees, A. et al. "Activation of soluble polysaccharides with 1-cyano-4-dimethylaminopyridinium tetrafluoroborate (CDAP) for use in protein-polysaccharide conjugates vaccines and immunological reagents. II. Selective crosslinking of proteins to CDAP-activated polysaccharides," *Vaccine 18*: 1273-81 (2000).

Shirota et al. "Regulation of Murine Airway Eosinophilia and Th2 Cells by Antigen-Conjugaed CpG Oligodeoxynucleotides as a Novel Antigen-Specific Immunomodulator," *J. Immunol. 164*: 5575-82 (2000).

Smith et al. "A Surface-Based Approach to DNA Computation," *J. Comp. Biol. 5*(2): 255-67 (1998).

Verheijen et al. "Incorporation of a 4-Hydroxy-N-acetylprolinol Nucleotide Analogue Improves the 3'-Exonuclease Stability of 2'-5'-Oligoadenylate-Antisense Conjugates," *Bioorg. Med. Chem. Lett. 10*: 801-4 (2000).

Wang et al. "Surface-based DNA computing operations: DESTROY and READOUT," *BioSystems 52*: 189-91 (1999).

hydrazine hydrazide semicarbazide thiosemicarbazide carbazide thiocarbazide carbonic acid dihydrazine hydrazine carboxylate hydroxylamine
or aminooxy aldehyde ketone $R_1$ and $R_2$ = alkyl, aromatic or heteroaromatic hydrazino X = NH  
oxyamino X = O carbonyl hydrazone X = NH  
oxime   X = O R' = hydrogen or aliphatic or aromatic moiety 5-1

5-2

1) DMF, 0.1 M phosphate
   0.15 M NaCl, pH 4.7

2) ion exchange HPLC 5-3 cyanine dyes

D = S, CMe$_2$;  A = H, SO$_3^-$, CH;  n = 1, 2 or 3;  R, R' = alkyl, aryl, heteroaryl, M-X rhodamines R = H, alkyl, aryl, heteroaryl, M-X fluoresceins R = H, OR, NR$_2$, alkyl, aryl, heteroaryl, M-X

SEQUENCE LISTING

```
<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: Synthetic Olignucleotide M13F complement 5'G

<400> SEQUENCE: 1
ggtcgtgact gggaaaac                                                      18

<210> SEQ ID NO 2
<211> LENGTH: 17
<212> TYPE: DNA
<213> ORGANISM: Artificial Sequence
```

-continued

```
<220> FEATURE:
<223> OTHER INFORMATION: Synthetic Olignucleotide M13F

<400> SEQUENCE: 2
gttttcccag tcacgac                                                    17

<210> SEQ ID NO 3
<211> LENGTH: 24
<212> TYPE: DNA
<213> ORGANISM: Artificial Sequence
<220> FEATURE:
<223> OTHER INFORMATION: Synthetic Olignucleotide M13F

<400> SEQUENCE: 3
agcccataac aatttcacac agga                                            24

<210> SEQ ID NO 4
<211> LENGTH: 16
<212> TYPE: DNA
<213> ORGANISM: Artificial Sequence
<220> FEATURE:
<223> OTHER INFORMATION: Synthetic Oligonucleotide TF3

<400> SEQUENCE: 4
atggaagaat ctctcc                                                     16

<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide Ferritin283

<400> SEQUENCE: 5
ggaacatgct gaaaactg                                                   18

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide b-actin300

<400> SEQUENCE: 6
tcaccaactg ggacgacatg                                                 20

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 19
<223> OTHER INFORMATION: n=5-((3-(4-formylbenzoyl)amino)propyn-1-yl)-2'-
      deoxycytidine

<400> SEQUENCE: 7
ggtcgtgact gggaaaacn                                                  19
```

US 7,173,125 B2

TRIPHOSPHATE OLIGONUCLEOTIDE MODIFICATION REAGENTS AND USES THEREOF

CROSS-REFERENCE TO RELATED APPLICATIONS

This application is a divisional of U.S. patent application Ser. No. 09/630,627 filed Aug. 1, 2000 now U.S. Pat. No. 6,686,461 to Schwartz et al., entitled "TRIPHOSPHATE OLIGONUCLEOTIDE MODIFICATION REAGENTS AND USES THEREOF. "The disclosure of the above-referenced application is incorporated herein in its entirety."

FIELD OF THE INVENTION

Monomers and methods for preparation, detection and immobilization of macromolecules, including biopolymers, and for preparation and detection of macromolecular conjugates are provided. The monomers for use in the methods provided herein include hydrazino, oxyamino and carbonyl substituted nucleoside triphosphates. Biopolymers, including oligonucleotides, possessing hydrazino, oxyamino or carbonyl modifications are also provided.

BACKGROUND OF THE INVENTION

Polymerase chain reaction (PCR) expression of oligonucleotides is a powerful tool in molecular biology. The PCR product is generally labeled to aid in detection. Various methods of direct and indirect labeling of the PCR product have been developed. Direct labeling involves the incorporation of a labeled monomer during enzymatic synthesis, while indirect labeling refers to post-synthetic introduction of the label.

For example, methods for direct labeling of PCR products are known (see, U.S. Pat. No. 5,242,756 and International Patent Application Publication No. WO 99/65993) In such methods, modified nucleoside triphosphates are incorporated into oligonucleotides during amplification; and conjugation of a xanthene or cyanine label to a nucleoside triphosphate is effected via an amide bond formed with the modified nucleoside triphosphates. Other methods involving conjugation of a biotin or metal chelating label to an oligonucleotide via an amide or hydrazide bond are used to form desired oligonucleotide-label conjugates (see, U.S. Pat. Nos. 4,707,440 and 4,889,798). Another method for indirect labeling of oligonucleotides involves incorporation of a boronic acid containing nucleoside triphosphate into an oligonucleotide during enzymatic synthesis. Complexation of this boronic acid modified oligonucleotide with a hydroxamic acid derivatized label provides the desired labeled oligonucleotide (see, U.S. Pat. No. 5,876,938).

These methods of oligonucleotide labelling, however, are limited by the lack of stability of the label to the amplification reaction conditions, the inability to selectively and specifically incorporate multiple labels, and the instability of succinimidyl esters. Preparation of activated functionalities, such as succinimidyl esters or maleimides, of labels can be costly, and not even possible in some instances, particularly under PCR conditions.

Thus, due to the limitations of currently available methods as described above, there is a need for efficient methods for labeling of oligonucleotides. Therefore, it is an object herein to provide monomers and methods for labeling of oligonucleotides without the need for post-synthetic modification of the oligonucleotide. It is also an object herein to provide monomers and methods for enzymatic synthesis of modified biopolymers, including oligonucleotides, that can be specifically labeled. A further object herein is to provide the resulting modified oligonucleotides.

SUMMARY OF THE INVENTION

Oligonucleotide monomers containing hydrazino, oxyamino, or carbonyl groups that can be incorporated into an oligonucleotide chain during enzymatic oligonucleotide synthesis are provided. Methods for immobilization and conjugation of biopolymer first components, particularly oligonucleotides, containing hydrazino, oxyamino, or carbonyl modifications are provided. The monomers are triphosphate nucleoside derivatives that can be incorporated into an oligonucleotide first component during enzymatic synthesis, including, but not limited to, synthesis by polymerase chain reactions (PCR), reverse trascriptases, including, but not limited to, AMV reverse transcriptase, MMLV reverse transcriptase and superscript reverse transcriptase, and polymerases, including, but not limited to, Taq polymerase, DNA plymerase, Klenow fragment and T4 DNA polymerase. The resulting first components can then be used for any purpose for which oligonucleotides are used. They are particularly suitable for conjugation to a second component or immobilizion on a surface. The monomers provided herein advantageously are readily incorporated into oligonucleotide chains, hence can be used in any application that involves or uses a nucleoside triphosphate, such as DNA and RNA sequencing, detecting, labeling and amplification methodologies. Monophosphate and diphoshate forms of the monomers as well as nucleic acid chains containing the incorporated monomers are provided.

The monomers provided herein are also useful as mass modifiers in DNA sequencing by mass spectrometry (see, e.g., U.S. Pat. Nos. 6,074,823 and 5,547,835). The monomers can be incorporated into oligonucleotides for the accurate determination of base composition (Muddiman et al. (1997) *Anal. Chem.* 69:1543), and for the scoring of single nucleotide polymorphisms (SNPs) (Chen. et al. (1999) *Anal. Chem.* 71:3118). The monomers can also be used to study the mechanisms by which ribozymes effect catalytic cleavage (Earnshaw et al. (2000) *Biochemistry* 39:6410). The monomers can be incorporated into antisense oligonucleotides to increase their resistance to enzymatic degradation (Verheijen et al. (2000) *Bioorg. Med. Chem. Lett.* 10:801), their overall potency (Flanagan et al. (1999) *Proc. Natl. Acad. Sci. USA* 96:3513) and the stability of their hybrids with the complementary RNA sequences (Compagno et al. (1999) *J. Biol. Chem.* 274:8191).

The monomers possess a triphosphate-ribose-nucleobase motif for recognition by the enzymatic catalyst.

Riboses for use in the monomers and methods herein are well known to those of skill in the art, and include, but are not limited to, fully hydroxylated sugars such as ribose, deoxyriboses such as 2-deoxyriboses, and dideoxy riboses such as 2,3-dideoxyribose.

Nucleobases for use in the monomers and methods herein are also well known to those of skill in the art, and include, but are not limited to, cytosines, uracils, adenines, guanines and thymines, and analogs thereof, including deaza analogs.

The monomers also possess, in addition to the triphosphate group, a protected or unprotected hydrazino, protected or unprotected oxyamino (—O—$NH_2$), or carbonyl moiety for formation of a hydrazone or oxime linkage with an appropriately modified surface or second component. The hydrazino moiety can be an aliphatic, aromatic or heteroaromatic hydrazine, semicarbazide, carbazide, hydrazide, thiosemicarbazide, thiocarbazide, carbonic acid dihydrazine or hydrazine carboxylate (see, FIG. 2). The protecting groups are salts of the hydrazino or oxyamino group, including but not limited to, mineral acid salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group known to those of skill in the art (see, e.g., Greene et al. (1999) *Protective Groups in Organic Synthesis* (3rd Ed.) (J. Wiley Sons, Inc.)). The carbonyl moiety can be any carbonyl containing group capable of forming a hydrazone or oxime linkage with one or more of the above hydrazino or oxyamino moieties. Preferred carbonyl moieties include aldehydes and ketones.

Second components include, but are not limited to, macromolcules, biopolymers as defined herein, polymers including, but not limited to, polyamines, polyamides, polyethers and polyethylene glycols, and other compounds of interest herein for use in assays, kits, diagnostic arrays, and the like, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that possess or are modified to possess a hydrazino, oxyamino or carbonyl group that is complementary to the carbonyl, oxyamino or hydrazino group of the oligonucleotide of formula (II) for formation of hydrazone or oxime linkage. Dendrimeric compounds that possess a plurality of detectable groups, including, but not limited to, reporter molecules, fluorophores, chromophores, fluorophore precursors and chromophore precursors, are also contemplated herein as second components. Fluorophore precursors and chromophore precursors are compounds that react with the hydrazino, oxyamino or carbonyl group of the modified oligonucleotide to form a fluorogenic or chromogenic group for analysis. Such groups are preferred due to the absence of background noise in the resulting assay. Preferred conjugates include those containing a hydrazone linkage.

In one-embodiment, the monomers for use in the methods provided herein are capture nucleoside triphosphates (cNTPs) that have formula (I):

$$P^1-S^1-B^1-M-X$$

or a derivative thereof, as defined herein, where $P^1$ is a triphosphate group, as defined herein; $S^1$ is a ribose, a deoxyribose or a dideoxyribose; $B^1$ is a nucleobase; X is a protected or unprotected hydrazino group, a protected or unprotected oxyamino group, or a carbonyl derivative, where the protecting group is a salt or any amino or hydrazino protecting group known to those of skill in the art; and M is a divalent group having any combination of the following groups, which can be combined in any order: arylene, heteroarylene, cycloalkylene, $C(R^1)_2$, $-C(R^1)=C(R^1)-$, $>C=C(R^2)(R^3)$, $>C(R^2)(R^3)$, $-C\equiv C-$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1-R^4$; each $M^1$ is a divalent group independently having any combination of the following groups, which groups can be combined in any order: a direct link, arylene, heteroarylene, cycloalkylene, $C(R^5)_2$, $-C(R^5)=C(R^5)-$, $>C=C(R^2)(R^3)$, $>C(R^2)(R^3)$, $-C\equiv C-$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1$, $R^2$, $R^3$, $R^4$, $R^5$, $R^6$, $R^7$, $R^8$, $R^9$ and $R^{10}$ are optionally substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

Macromolecutions, particularly biopolymers, including oligonucleotides, that are modified by incorporation of the above monomers are provided. Thus, in certain embodiments, provided herein are oligonucleotide analogs of formula (II):

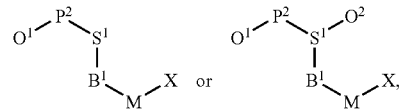

or a derivative thereof, where $O^1$ and $O^2$ are each independently oligonucleotides or analogs thereof, such as protein nucleic acids (PNAs); $P^2$ is a phosphodiester group, resulting from the coupling of a compound of formula (I) with $O^1$ or analog thereof; and $S^1$, $B^1$, M and X are selected as above.

Such oligonucleotide analogs are useful as antisense drugs, cis-elements acting as regulators of gene expression, and substrates for RNA binding proteins such as HIV-1 Rev and Tat (see, e.g., Agrawal (1999) *Biochim. Biophys. Acta*

1489:53; Crooke (1999) *Biochim. Biophys. Acta* 1489:31; Gryaznov (1999) *Biochim. Biophys. Acta* 1489:131; and Morishita (2000) *Nipp. Yakuri. Zass.* 115:123).

Oligonucleotides covalently immobilized on a solid surface, as described herein, are also provided. The oligonucleotides are of formula (II), and are immobilized through a covalent hydrazone or oxime linkage. The solid surface is modified to possess a hydrazino, oxyamino, or carbonyl group that is complementary to the hydrazino, oxyamino or carbonyl moiety of the oligonucleotide of formula (II) for formation of a hydrazone or oxime linkage. In preferred embodiments, the oligonucleotides are immobilized through a covalent hydrazone linkage.

The immobilized oligonucleotides, as well as non-immobilized forms, are useful for a variety of purposes known to those of skill in the art, including, but not limited to, preparation of microarrays, diagnostic probe assays, DNA or RNA amplification, for example by solid phase polymerase chain reactions (PCR), molecular computing (see, e.g., Adleman (1994) *Science* 266:1021–1024; Kari (1997) *Mathematical Intelligencer* 19:9–22; Frutos et al. (1997) *Nucleic Acids Res.* 25:4748; Smith et al. (1998) *J. Comp. Biol.* 5:255; Liu et al. (1998) *J. Comp. Biol.* 5:267; Frutos et al. (1998) *J. Am. Chem. Soc.* 120:10277; Wang et al. (1999) *Biosystems* 52:189–191; Liu et al. (1–999) *Biosystems* 52:25–33; Liu et al. (2000) *Nature* 403:175–179; European Patent Application Publication No. EP 0 772 135; Reed et al. (June 2000) *Scientific American*:86–93), molecular addressing (Niemeyer et al. (1994) *Nucl. Acids Res.* 22(25):5530–5539), DNA and RNA sequencing methods, including mass spectrometry methods (see, e.g., U.S. Pat. Nos. 6,074,823 and 5,547,835), nucleic acid diagnostics, including SNP and other polymorphism analyses and detection methods, and in studying the molecular electronics of DNA (see, e.g., U.S. Pat. Nos. 6,071,699, 6,066,448, 5,952, 172 and 5,824,473).

The oligonucleotides can also be used in PCR-based sequencing methods, particularly solid phase sequencing methods using the immobilized oligonucleotides (Mustajoki et al. (1997) *Genome Res.* 7:1054). They can also be used to measure the interaction forces between single strands of DNA (Lee et al. (1994) *Science* 266:771), in solid phase-mediated transfection of oligonucleotides (Bielinska et al. (2000) *J. Biomaterials* 21:877), and in solid phase cloning to create libraries suitable for direct solid phase sequencing (Hultman et al. (1994) *J. Biotechnol.* 35:229). The immobilized oligonucleotides can also be used in DNA chip technology to create arrays of oligonucleotides which are used to compare the qualitative and quantitative characteristics of gene expression profiles, mutations, insertions and deletions in normal and diseased states (De Benedetti et al. (2000) *Int. J. Biol. Markers* 15:1). They can also be used to identify and characterize the DNA binding site of DNA binding proteins (Roth et al. (1995) *EMBO J.* 14:2106; Carlsson et al. (1995) *Anal. Biochem.* 232:172). Immobilized oligonucleotides bound to Sephacryl S-500 particles via a CNBr-activation procedure can be used to assemble extended DNA duplexes by phosphorylation, ligation and restriction enzyme digestion of assemblies of annealed oligonucleotides in solid phase (Hostomsky et al. (1987) *Nucleic Acids Symp. Ser.* 18:241). The immobilized oligonucleotides can also be used in PCR, RT-PCR (Kozwich et al. (2000) *Appl. Environ. Microbiol.* 66:2711; Blomqvist et al. (1999) *J. Clin. Microbiol.* 37:2813), transcription (Marble et al. (1995) *Biotechnol. Prog.* 11:393; Fujita et al. (1993) *Biotechniques* 14:608), ligation reactions (Filippov et al. (1990) *Bioorg. Khim.* 16:1045), and in studying DNA repair mechanisms (Salles et al. (1999) *Biochimie* 81:53).

In embodiments where X of the modified oligonucleotide is a hydrazino or oxyamino group, the solid surface can be modified to possess an epoxide, α-bromocarbonyl, maleimide, maleic anhydride, isothiocyanate or isocyanate group. Such solid surfaces can be prepared by methods provided herein or other methods well known to those of skill in the art. For example, reaction of pentafluorophenyl 4-isothiocyanatobenzoate with an amino solid surface results in formation of an isothiocyanato modified solid surface. Some of these surfaces are commercially available from, e.g., Pierce (Rockford, Ill.), SINTEF Applied Chemistry (Trondheim, Norway), Rapp Polymere Gmbh (Tubingen, Germany), and Dyno Particles AS (Trondheim, Norway). Reaction of the hydrazino or oxyamino group of the modified oligonucleotide with the epoxide, α-bromocarbonyl, maleimide, maleic anhydride, isothiocyanate or isocyanate group of the solid surface results in covalent attachment of the oligonucleotide to the solid surface.

In certain embodiments, particularly where X is an oxyamino group,: the immobilized oligonucleotides are selected such that the solid surface is not modified with an aldehyde or epoxide group.

Oligonucleotide conjugates are provided. The conjugates are prepared from the modified oligonucleotide first components of formula (II). The modified oligonucleotide of formula (II) is reacted with a complementary derivative of a second component to form a hydrazone or oxime covalent linkage. The second components include, but are not limited to, biopolymers as defined herein, polymers including, but not limited to, polyamines, polyamides, polyethers and polyethylene glycols, and other compounds of interest herein for use in assays, kits, diagnostic arrays, and the like, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that possess or are modified to possess a hydrazino, oxyamino or carbonyl group that is complementary to the carbonyl, oxyamino or hydrazino group of the oligonucleotide of formula (II) for formation of hydrazone or oxime linkage. Dendrimeric compounds that possess a plurality of detectable groups, including, but not limited to, reporter molecules, fluorophores, chromophores, fluorophore precursors and chromophore precursors, are also contemplated herein as second components. Fluorophore precursors and chromophore precursors are compounds that react with the hydrazino, oxyamino or carbonyl group of the modified oligonucleotide to form a fluorogenic or chromogenic group for analysis. Such groups are preferred due to the absence of background noise in the resulting assay. Preferred conjugates include those containing a hydrazone linkage.

In embodiments where X is a hydrazino or oxyamino group, the second component can be modified to possess an epoxide, α-bromocarbonyl, maleimide, maleic anhydride, isothiocyanate or isocyanate group. Such second components can be prepared by methods provided herein or by other methods well known to those of skill in the art. For example, reaction of pentafluorophenyl 4-isothiocyanatobenzoate with an amino or hydroxy group of a second component, such as a protein or oligosaccharide, results in formation of an isothiocyanato modified second component.

Reaction of the hydrazino or oxyamino group of the modified oligonucleotide with the epoxide, α-bromocarbonyl, maleimide, maleic anhydride, isothiocyanate or isocyanate group of the second component results in covalent attachment of the oligonucleotide to the second component to form the conjugates provided herein.

In certain embodiments herein, the oligonucleotide conjugates are selected with the proviso that the covalent linkage is not an acyl hydrazone (—C(O)NHNH=). In preferred embodiments, the oligonucleotide conjugates are prepared from modified oligonucleotides of formula (II) where $P^2$ is not a phosphoramidate. In other embodiments, the oligonucleotide conjugates are selected with the proviso that the second component is not a protein, particularly a glycoprotein, more particularly an immunoglobulin.

The modified oligonucleotides provided herein can also be conjugated to ligands such as growth factors, membrane-active bacterial proteins and asialoglycoproteins as delivery strategies for antisense therapy and gene therapy (see, e.g., Perales et al. (1994) *Eur. J. Biochem.* 226:255; Cristiano et al. (1996) *Cancer Gene Ther.* 3:4; Hoganson et al. (1998) *Hum. Gene Ther.* 9:2565; Gottschalk et al. (1995) *Gene Ther.* 2:498; Lu et al. (1994) *J. Nucl. Med.* 35:269). Oligonucleotide-antigen conjugates can be used as immunomodulators in regulating airway eosinophilia in bronchial asthma (Shirota et al. (2000) *J. Immunol.* 164:5575). Oligonucleotide probes conjugated to fluorescent molecules are used in fluorescence in situ hybridization (FISH) for chromosome classification and the detection of chromosome aberrations (Pinkel et al. (1986) *Proc. Natl. Acad. Sci. USA* 83:2934). Oligonucleotide conjugates are also used to study the mechanics of DNA hybridization, and to investigate protein-DNA contacts of DNA binding proteins (Lannutti et al. (1996) *Biochemistry* 35:9821; Brown et al.(1997) *Curr. Opin. Biotechnol.* 8:45).

Importantly, the immobilized oligonucleotides or oligonucleotide conjugates provided, herein can be formed under aqueous conditions without the need for additional reagents, such as a reducing agent.

Methods for the attachment of hydrazino, oxyamino, or carbonyl modified oligonucleotides of formula (II) to appropriately modified surfaces, as described herein, are provided. The attachment is via a covalent hydrazone or oxime bond formed from the hydrazino, oxyamino, or carbonyl group of the modified oligonucleotide and a complementary carbonyl, oxyamino or hydrazino modified surface provided herein (see, FIG. 1).

Methods for the conjugation of oligonucleotide first components to second components, including, but not limited to, biopolymers as defined herein, polymers including, but not limited to, polyamines, polyamides, polyethers and polyethylene glycols, and other compounds of interest herein for use in assays, kits, diagnostic arrays, and the like, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that possess or are modified to possess a hydrazino, oxyamino or carbonyl group that is complementary to the carbonyl, oxyamino or hydrazino group of the oligonucleotide of formula (II) for formation of hydrazone or oxime linkage, are provided. Dendrimeric compounds that possess a plurality of detectable groups, including, but not limited to, reporter molecules, fluorophores, chromophores, fluorophore precursors and chromophore precursors, are also contemplated herein as second components. Fluorophore precursors and chromophore precursors are compounds that react with the hydrazino, oxyamino or carbonyl group of the modified oligonucleotide to form a fluorogenic or chromogenic group for analysis.

In particular, methods for conjugation of a hydrazino, oxyamino, or carbonyl modified oligonucleotide of formula (II) with an appropriately modified second component are provided. The conjugation is achieved through a covalent hydrazone or oxime bond formed from the hydrazino, oxyamino or carbonyl group of the modified oligonucleotide and a second component possessing a complementary carbonyl, oxyamino or hydrazino group.

In all embodiments herein, it is preferred that one, more preferably both, of the reactive partners (e.g., the hydrazino, oxyamino or carbonyl groups) are aromatic or heteroaromatic. Thus, in preferred embodiments, the compounds of formula (I) will be aryl or heteroaryl hydrazino or oxyamino derivatives, or aryl or heteroaryl carbonyl derivatives. In more preferred embodiments, the coupling partner (e.g., the modified solid surface or the second component) will also possess an aryl or heteroaryl hydrazino or oxyamino group, or an aryl or heteroaryl carbonyl group. Hydrazone and oxime linkages formed from these preferred groups are more stable than the corresponding aliphatic hydrazone and oxime linkages, and thus are more preferred in certain applications.

A composition, comprising one or more nucleoside triphosphates and a monomer, is provided herein. Methods using the composition to synthesize nucleic acid molecules that include the monomers provided herein incorporated into the chains are provided. Nucleic acid molecules (i.e. oligonucleotides) in which the monomers provided herein are at the end are also provided; these are produced by providing the monomers as chain terminators, such as dideoxynucleotides.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents, patent applications and publications referred to throughout the disclosure herein are incorporated by reference in their entirety. In the event that there are a plurality of definitions for term herein, those in this section prevail.

Figure 1:
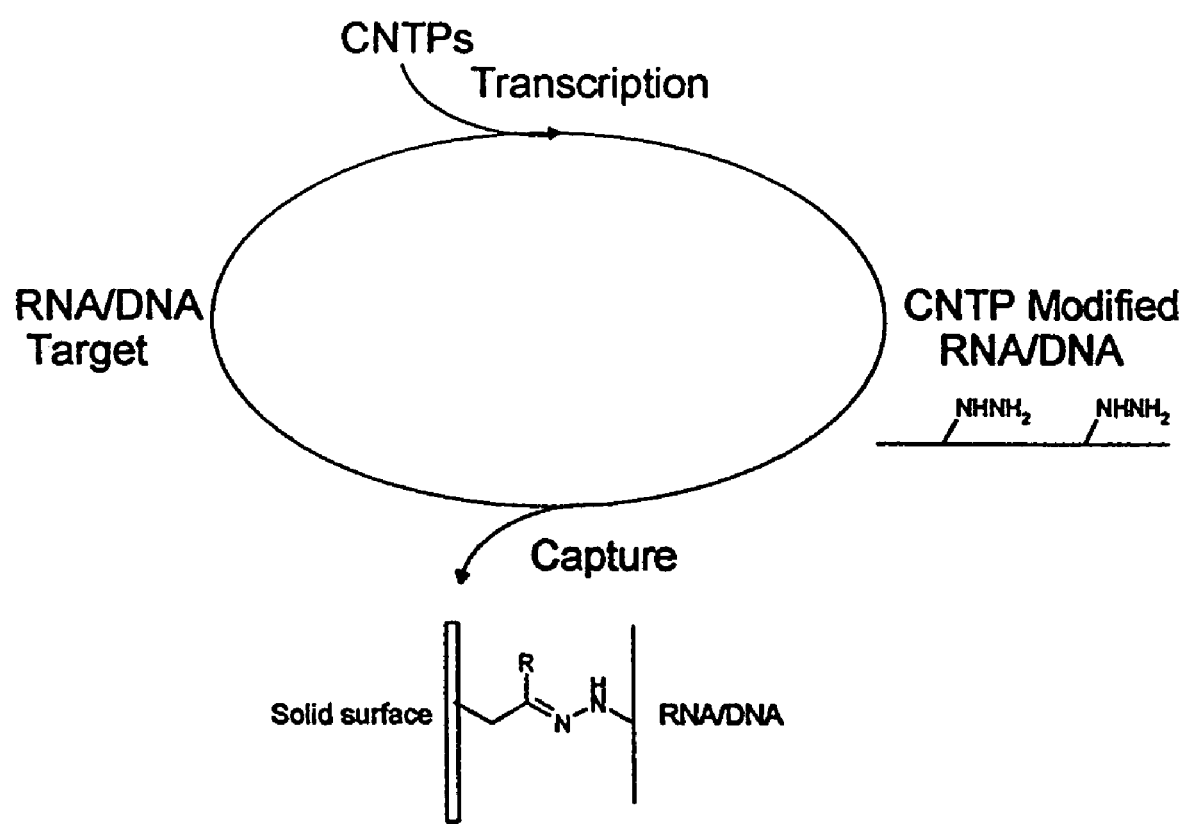
FIG. 1 illustrates incorporation of the capture nucleoside triphosphate (CNTP) monomers provided herein into an RNA/DNA target to form a modified RNA/DNA and capture of the modified RNA/DNA on a solid surface.
Figure 2:
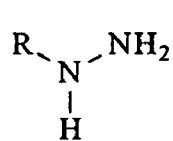
FIG. 2 illustrates hydrazino and oxyamino derivatives provided herein.
Figure 2:
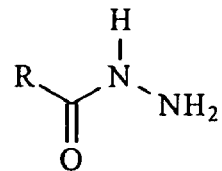
Figure 2:
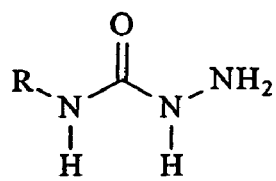
Figure 2:
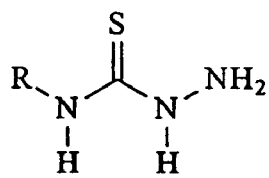
Figure 2:
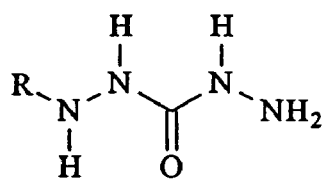
Figure 2:
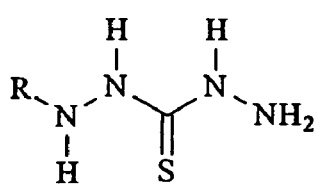
Figure 2:
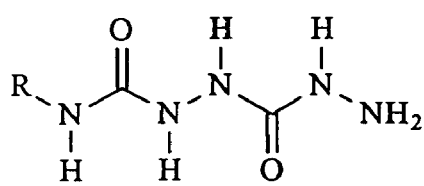
Figure 2:
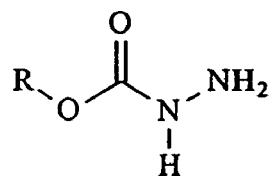
Figure 2:
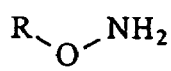
Figure 3:
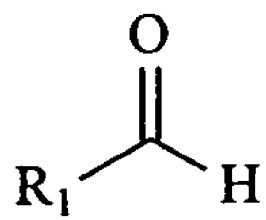
FIG. 3 illustrates carbonyl groups exemplified herein.
Figure 3:
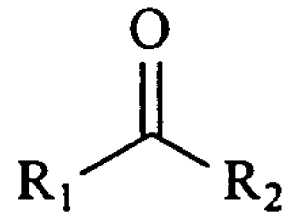
Figure 4:
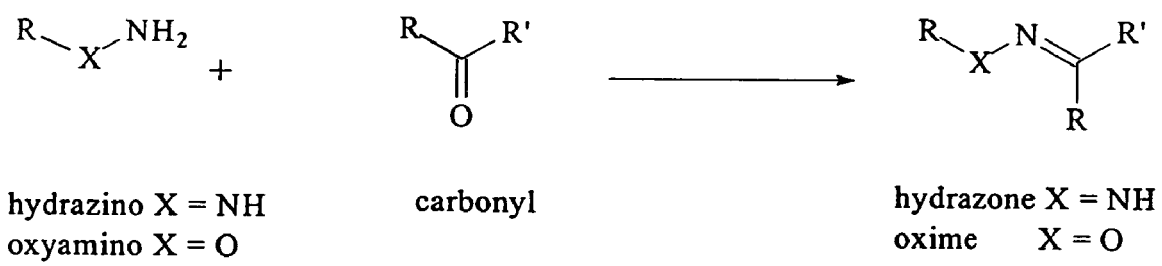
FIG. 4 shows the immobilization of a hydrazino or oxyamino modified oligonucleotide on a carbonyl modified solid support.

As used herein, "hydrazino groups" include, but are not limited to, hydrazines, hydrazides, semicarbazides, carbazides, thiosemicarbazides, thiocarbazides, hydrazine carboxylates and carbonic acid hydrazines (see, e.g., FIG. 2).

As used herein, hydrazone linkages include, but are not limited to, hydrazones, acyl hydrazones, sermicarbazones, carbazones, thiosemicarbazones, thiocarbazones, hydrazone carboxylates and carbonic acid hydrazones.

As used herein, an oxyamino group has the formula —O—NH$_2$. An oxime has the formula —O—N═R.

As used herein, carbonyl-based derivatives include, but are not limited to, ketones and aldehydes.

As used herein, a "triphosphate group" refers to (HO)P(O)(O$^-$)—O—P(O)(O$^-$)—O—P(O)(O$^-$)—.

As used herein, a protected hydrazino or a protected oxyamino group refers to a hydrazino or oxyamino group that has been derivatized as a salt of the hydrazino or oxyamino group, including but not limited to, mineral acid salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group known to those of skill in the art (see, e.g., Greene et al. (1999) *Protective Groups in Organic Synthesis* (3rd Ed.) (J. Wiley Sons, Inc.)). Preferred amino and hydrazino protecting groups herein include, but are not limited to, amino or hydrazino protecting groups useful in the synthesis of oligonucleotides, more preferably monomethoxytrityl (MMT), dimethoxytrityl (DMT), 9-fluorenylmethoxycarbonyl (FMOC), acetyl, trifluoroacetyl (TFA), benzoyl, or a hydrazone that is cleaved under mild acidic conditions (e.g., 100 mM acetate, pH 4.5–5.5) including, but not limited to, a hydrazone formed from a flower aliphatic aldehyde or ketone, preferably from acetone, cyclohexanone, propanal or 2-butanone.

As used herein, an oligonucleotide is a nucleic acid, including, but not limited to, a ribonucleic acid (RNA), a deoxyribonucleic acid (DNA), and analogs thereof such as a protein nucleic acid (PNA), of any length, including chromosomes and genomic material, such as PCR products or sequencing reaction products, preferably DNA including double and single stranded forms. Single stranded forms of the oligonucleotides are also provided.

As used herein, a conjugate is a compound containing two components covalently linked together For example, a first component, e.g., an oligonucleotide, is conjugated through a covalent hydrazone linkage to a second component, as defined herein, to form a conjugate.

As used herein, a biopolymer is any compound found in nature, or derivatives thereof, made up of monomeric units. Biopolymers include, but are not limited to, oligonucleotides, peptides, peptide, nucleic acids (PNAs), glycoproteins and oligosaccharides. Thus, the monomeric units include, but are not limited to, nucleotides, nucleosides, amino acids, PNA monomers, monosaccharides, and derivatives thereof.

As used herein, a macromolecule refers to a molecule of colloidal size (i.e., of high molecular weight), including, but not limited to, proteins, polynucleic acids, polysaccharides and carbohydrates.

As used herein, complementary reactive groups are those that, when reacted together, form a covalent linkage, including, but not limited to, a hydrazone or oxime linkage. Thus, a hydrazino group, as defined herein, is complementary to a carbonyl group. An oxyamino group is also complementary to a carbonyl group.

As used herein, a reporter molecule refers to a molecule, such as an enzyme or indicator, which is capable of generating a detectable signal (e.g., by colorimetric, chemiluminescent, bioluminescent, fluorescent, or potentiometric means) when contacted with a suitable substrate-under appropriate reaction conditions. Exemplary reporter enzymes include, but are not limited to, alkaline phosphatase, horseradish peroxidase, β-galactosidase, aryl esterase, sulfatase and urease.

As used herein, a nucleobase is a heterocyclic moiety that is found in naturally occurring oligonucleotides, including ribonucleic acids (RNA) and deoxyribonucleic acids. (DNA), and analogs thereof, including deaza analogs. Preferred nucleobases include, but are not limited to, cytosines, uracils, adenines, guanines and thymines, and analogs thereof including deaza analogs.

As used herein, a derivative of a compound includes a salt, ester, enol ether, enol ester, solvate or hydrate thereof that can be readily prepared by those of skill in this art using known methods for such derivatization. Salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Enol ethers include, but are not limited to, derivatives of formula C═C(OR) where R is hydrogen, alkyl, alkenyl, alkynyl, aryl, heteroaryl, aralkyl, heteroaralkyl, cycloalkyl ar heterocyclyl. Enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl ar heterocyclyl. Solvates and hydrates are complexes of a compound with one or more solvent or water molecule, preferably 1 to about 100, more preferably 1 to about 10, most preferably one to about 2, 3 or 4, solvent or water molecules.

It is to be understood that the compounds provided herein can contain chiral centers. Such chiral centers can be of either the (R) or (S) configuration, or can be a mixture thereof. Thus, the compounds provided herein can be enantiomerically pure, or be stereoisomeric or diastereomeric mixtures. In the case of amino acid residues, such residues can be of either the L- or D-form. The preferred configuration for naturally occurring sugar residues is D.

As used herein, alkyl, alkenyl and alkynyl carbon chains, if not specified, contain from 1 to 20 carbons, preferably 1 to 16 carbons, and are straight or branched. Alkenyl carbon chains of from 2 to 20 carbons preferably contain 1 to 8 double bonds, and the alkenyl carbon chains of 1 to 16 carbons preferably contain 1 to 5 double bonds. Alkynyl carbon chains of from 2 to 20 carbons preferably contain 1 to 8 triple bonds, and the alkynyl carbon chains of 2 to 16 carbons preferably contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, pentyl and isohexyl. The alkyl, alkenyl and alkynyl groups, unless otherwise specified, can be optionally substituted, with one or more groups, preferably alkyl group substituents that can be the same or different. As used herein, lower alkyl, lower alkenyl, and lower alkynyl refer to carbon chains having less than about 6 carbons. As used herein, "alk(en)(yn)yl" refers to an alkyl group containing at least one double bond and at least one triple bond.

As used herein, an "alkyl group substituent" includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups containing from 5 to 19 carbon atoms. Aryl groups include, but are not limited to groups, such as fluorenyl, substituted fluorenyl, phenyl, substituted phenyl, naphthyl and substituted naphthyl, in which the substituent is lower alkyl, halogen, or lower alkoxy.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, pseudohalo, cyano, hydroxy, haloalkyl and polyhaloalkyl, preferably halo lower alkyl, especially trifluoromethyl, formyl, alkylcarbonyl, arylcarbonyl that is optionally substituted with 1 or more; preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "cycloalkyl" refers to a saturated mono- or multicyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups can preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups can be composed of one ring or two or more rings which can be joined together in a fused, bridged or spiro-connected fashion, and can be optionally substituted with one or more alkyl group substituents. "Cycloalk(en)(yn)yl" refers to a cylcoalkyl group containing at least one double bond and at least one triple bond.

As used herein, "heteroaryl" refers to a monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroaryl can be optionally substituted with one or more, preferably 1 to 3, aryl group substituents. The heteroaryl group can be optionally fused to a benzene ring. Exemplary heteroaryl groups include, for example, furyl, imidazolyl, pyrrolidinyl, pyrimidinyl, tetrazolyl, thienyl, pyridyl, pyrrolyl, N-methylpyrrolyl, quinolinyl and isoquinolinyl, with pyridyl and quinolinyl being preferred.

As used herein, "heterocyclic" refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle can be optionally substituted with one or more, preferably 1 to 3 aryl group substituents. Preferred substituents of the heterocyclic group include hydroxy, amino, alkoxy containing 1 to 4 carbon atoms, halo lower alkyl, including trihalomethyl, such as trifluoromethyl, and halogen. As used herein, the term heterocycle can include reference to heteroaryl.

As used herein, the nomenclature alkyl, alkoxy, carbonyl, etc. are used as is generally understood by those of skill in this art. For example, as used herein alkyl refers to saturated carbon chains that contain one or more carbons; the chains can be straight or branched or include cyclic portions or be cyclic. As used herein, alicyclic refers to aryl groups that are cyclic.

Where the number of any given substituent is not specified (e.g., "haloalkyl"), there can be one or more substituents present. For example, "haloalkyl" can include one or more of the same or different halogens. As another example, "$C_{1-3}$alkoxyphenyl" can include one or more of the same or different alkoxy groups containing one, two or three carbons.

As used herein, "halogen" or "halide" refers to F, Cl, Br or I.

As used herein, pseudohalides are compounds that behave substantially similar to halides. Such compounds can be used in the same manner and treated in the same, manner as halides ($X^-$, in which X is a halogen, such as Cl or Br). Pseudohalides include, but are not limited to, cyanide, cyanate, thiocyanate, selenocyanate, trifluoromethoxy, trifluoromethyl and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_3$—.

As used herein, "carboxy" refers to a divalent radical, —C(O)O—.

As used herein, "aminocarbonyl" refers to —C(O)NH$_2$.

As used herein, "alkylaminocarbonyl" refers to —C(O) NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR.

As used herein, "diarylaminocarbonyl" refers to —C(O)NRR' in which R and R' are independently selected from aryl, preferably lower aryl, more preferably phenyl.

As used herein, "aralkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "alkylthio" refer to RO— and RS—, in which R is alkyl, preferably lower alkyl.

As used herein, "aryloxy" and "arylthio" refer to RO— and RS—, in which R is aryl, preferably lower aryl, more preferably phenyl.

As used herein, "alkylene" refers to a straight, branched or cyclic, preferably straight or branched, divalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There can be optionally inserted along the alkylene group one or more oxygen, sulphur or substituted or unsubstituted nitrogen atoms, where the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, divalent aliphatic hydrocarbon group, preferably having from 2 to about 20 carbon atoms and at least one double bond, more preferably 1 to 12 carbons, even more preferably lower alkenylene. The alkenylene group is optionally substituted with one or more "alkyl group substituents." There can be optionally inserted along the alkenylene group one or more oxygen, sulphur or substituted or unsubstituted nitrogen atoms, where the nitrogen substituent is alkyl as previously described. Exemplary alkenylene groups include —CH=CH—CH=CH— and —CH=CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, divalent aliphatic hydrocarbon group, preferably having from 2 to about 20 carbon atoms and at least one triple bond, more preferably 1 to 12 carbons, even more preferably lower alkynylene. The alkynylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—CH$_2$—. The term "lower alkynylene" refers to alkynylene groups having 2 to 6 carbons. Preferred alkynylene groups are lower alkynylene, with alkynylene of 3 to 4 carbon atoms being particularly preferred.

As used herein, "alk(en)(yn)ylene" refers to a straight, branched or cyclic, preferably straight or branched, divalent aliphatic hydrocarbon group, preferably having from 2 to about 20 carbon atoms and at least one triple bond, and at least one double bond; more preferably 1 to 12 carbons, even more preferably lower alk(en)(yn)ylene. The alk(en)(yn)ylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alk(en)(yn)ylene groups include —C=C—(CH$_2$)$_n$—C≡C—, where n is 1 or 2. The term "lower alk(en)(yn)ylene" refers to alk(en)(yn)ylene groups having up to 6 carbons. Preferred alk(en)(yn)ylene groups are lower alk(en)(yn)ylene, with alk(en)(yn)ylene of 4 carbon atoms being particularly preferred.

As used herein, "arylene" refers to a monocyclic or polycyclic, preferably monocyclic, divalent aromatic group, preferably having from 5 to about 20 carbon atoms and at least one aromatic ring, more preferably 5 to 12 carbons, even more preferably lower arylene. The arylene group is optionally substituted with one or more "alkyl group substituents." There can be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a divalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroarylene group can be optionally substituted with one or more, preferably 1 to 3, aryl group substituents.

As used herein, "alkylidene" refers to a divalent group, such as =CR'R", which is attached to one atom of another group, forming a double bond. Exemplary alkylidene groups are methylidene (=CH$_2$) and ethylidene (=CHCH$_3$). As used herein, "aralkylidene" refers to an alkylidene group in which either R' or R" is and aryl group.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the group —SO$_2$NHNH—. "Hydrazide" refers to the divalent group —C(O)NHNH—. "Azo" refers to the divalent group —N=N—. "Hydrazinyl" refers to the divalent group —NH—NH—.

As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid.

As used herein, when any particular group, such as phenyl or pyridyl, is specified, this means that the group is unsubstituted or is substituted. Preferred substituents where not specified are halo, halo lower alkyl, and lower alkyl.

As used herein, a composition refers to any mixture of two or more products or compounds. It can be a solution, a suspension, liquid, powder, a paste, aqueous, non-aqueous or any combination thereof.

As used herein, a combination refers to any association between two or more items.

As used herein, fluid refers to any composition that can flow. Fluids thus encompass compositions that are in the form of semi-solids, pastes, solutions, aqueous mixtures, gels, lotions, creams and other such compositions.

As used herein, substantially identical to a product means sufficiently similar so that the property of interest is sufficiently unchanged so that the substantially identical product can be used in place of the product.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11, 942).

A. Nucleoside Triphosphate Monomers

Nucleoside triphosphate monomers are provided. The monomers are incorporated into oligonucleotide first components during enzymatic synthesis. The resulting modified oligonucleotides are readily immobilized or conjugated through a hydrazone or oxime linkage. The reagents possess a triphosphate-ribose-nucleobase motif for recognition by the enzymatic catalyst.

The monomers also possess, in addition to the triphosphate-ribose-nucleobase motif, a protected or unprotected hydrazino, protected or unprotected oxyamino, or a carbonyl moiety for formation of a hydrazone or oxime linkage with an appropriately modified surface or second component. The hydrazino moiety can be an aliphatic, aromatic or heteroaromatic hydrazine, semicarbazide, carbazide, hydrazide, thiosemicarbazide, thiocarazide, carbonic acid dihydrazine or hydrazine carboxylate (see, FIG. 2). The protecting groups are salts of the hydrazino or oxyamino group, or any amino or hydrazino protecting groups known to those of skill in the art (see, e.g., Greene et al. (1999) *Protective Groups in Organic Synthesis* (3rd Ed.) (J. Wiley Sons, Inc.)). The carbonyl moiety can be any carbonyl containing group capable of forming a hydrazone or oxime linkage with one or more of the above hydrazino or oxyamino moieties. Preferred carbonyl moieties include aldehydes and ketones.

In one embodiment, the monomers for use in the methods provided herein have formula (I):

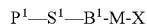

or a derivative thereof, as defined herein, where $P^1$ is a triphosphate group, as defined herein, and is preferably at the 5' position of $S^1$; X is a protected or unprotected hydrazino group; $S^1$ is a ribose, deoxyribose including a 2'-deoxyribose, or a dideoxyribose including a 2',3'-dideoxyribose; $B^1$ is a nucleobase; and M is a divalent group having any combination, preferably 1–2000, more preferably 1–1000, particularly 1–100, most preferably 1–50 or 1–25 or 1–10, of the following groups, which can be combined in any order: arylene, heteroarylene, cycloalkylene, $C(R^1)_2$, —$C(R^1)$=$C(R^1)$—, >C=$C(R^2)(R^3)$, >$C(R^2)(R^3)$, —C≡C—, O, $S(A)_a$, $P(D)_b(R^1)$, $P(D)_b(ER^1)$, $N(R^1)$, >$N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1$-$R^4$; each $M^1$ is a divalent group independently having any combination of the following groups, which groups can be combined in any order: a direct link, arylene, heteroarylene, cycloalkylene, $C(R^5)_2$, —$C(R^5)$=$C(R^5)$—, >C=$C(R^2)(R^3)$, >$C(R^2)(R^3)$, —C≡C—, O, $S(A)_a$, $P(D)_b(R^5)$, $P(D)_b(ER^5)$, $N(R^5)$, $N(COR^5)$, >$N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1$, $R^2$, $R^3$, $R^4$, $R^5$, $R^6$, $R^7$, $R^8$, $R^9$ and $R^{10}$ can be substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In another embodiment, the monomers for use in the methods provided herein have formula (I):

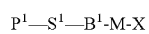

or a derivative thereof, as defined herein, where $P^1$ is a triphosphate group, as defined herein, and is preferably at the 5' position of $S^1$; X is a protected or unprotected oxyamino group; $S^1$ is a ribose, a deoxyribose including a 2'-deoxyribose, or a dideoxyribose including a 2',3'-dideoxyribose; $B^1$ is a nucleobase; and M is a divalent group having any combination, preferably 1–2000, more preferably 1–1000, particularly 1–100, most preferably 1–50 or 1–25 or 1–10, of the following groups, which can be combined in any order: arylene, heteroarylene, cycloalkylene, $C(R^1)_2$, $—C(R^1)=C(R^1)—$, $>C=C(R^2)(R^3)$, $>C(R^2)(R^3)$, $—C≡C—$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1$-$R^4$; each $M^1$ is a divalent group independently having any combination of the following groups, which groups can be combined in any order: a direct link, arylene, heteroarylene, cycloalkylene, $C(R^5)_2$, $—C(R^5)=C(R^5)—$, $>C=C(R^2)(R^3)$, $>C(R^2)(R^3)$, $—C≡C—$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1$, $R^2$, $R^3$, $R^4$, $R^5$, $R^6$, $R^7$, $R^8$, $R^9$ and $R^{10}$ can be substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In another embodiment, the monomers for use in the methods provided herein have formula (I):

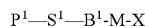

or a derivative thereof, as defined herein, where $P^1$ is a triphosphate group, as defined herein, and is preferably at the 5' position of $S^1$; X is a carbonyl group; $S^1$ is a ribose, a deoxyribose including 2'-deoxyribose, or a dideoxyribose including 2',3'-dideoxyribose; $B^1$ is a nucleobase; and M is a divalent group having any combination, preferably 1–2000, more preferably 1–1000, particularly 1–100, most preferably 1–50 or 1–25 or 1–10, of the following groups, which can be combined in any order: arylene, heteroarylene, cycloalkylene, $C(R^1)_2$, $—C(R^1)=C(R^1)—$, $>C=C(R^2)(R^3)$, $>C(R^2)(R^3)$, $—C≡C—$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1$-$R^4$; each $M^1$ is a divalent group independently having any combination of the following groups, which groups can be combined in any order: a direct link, arylene, heteroarylene, cycloalkylene, $C(R^5)_2$, $—C(R^5)=C(R^5)—$, $>C=C(R^2)(R^3)$, $>C(R^2)(R^3)$, $—C≡C—$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or O; and E is S, O or $NR^5$; $R^4$ and $R^5$ are each independently selected from among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1$, $R^2$, $R^3$, $R^4$, $R^5$, $R^6$, $R^7$, $R^8$, $R^9$ and $R^{10}$ can be substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In certain embodiments, the reagents for use in the methods provided herein are triphosphates that have formula (I):

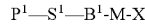

or a derivative thereof, wherein $S^1$ is ribose, 2'-deoxyribose, or 2',3'-dideoxyribose; X is a protected or unprotected hydrazino, protected or unprotected oxyamino, or a carbonyl group; $B^1$ is a cytosine, uracil, adenine, guanine or thymine, or an analog thereof, including, but not limited to, 7-deazaadenine, 7-deazaguanine and 7-deazahypoxanthine; and P¹ and M are selected as above.

M preferably has 1–2000, more preferably 1–1000, particularly 1–100, most preferably 1–50 or 1–25 or 1–10 of the groups as defined above. In certain embodiments, M has 1–50, preferably 1–25, more preferably 1–10 of the following groups, which can be combined in any order: arylene, heteroarylene, $C(R^1)_2$, —$C(R^1)$=$C(R^1)$—, —C≡C—, O, $S(A)_a$, $N(R^1)$, $N(COR^1)$ and C(E); where a is 0, 1 or 2; A is O or $NR^1$; and E is S, O or $NR^1$; where $R^1$ is as defined above. In more preferred embodiments, M has 1–10 of the following groups, which can be combined in any order: heteroarylene, $C(R^1)_2$, —C≡C—, $N(R^1)$ and C(E); where E is S, O or $NR^1$; where $R^1$ is as defined above. In other embodiments, M has 1–10 of the following groups, which can be combined in any order: arylene, $C(R^1)_2$, —C≡C—, $N(R^1)$ and C(E); where E is S, O or $NR^1$; where $R^1$ is as defined above. $R^5$ is preferably hydrogen; and E is preferably oxygen. In further embodiments, M has 1–10 of the following groups, which can be combined in any order: $C(R^1)_2$, —C≡C—, $N(R^1)$ and C(E); where E is S, O or $NR^1$; where $R^1$ is as defined above. In these embodiments, the heteroarylene groups of M are preferably monocyclic or fused bicyclic divalent groups, more preferably monocyclic divalent groups, including, but not limited to, thienylene, furylene, pyrrolylene including 2,3-, 2,4- and 2,5-pyrrolylene, pyridylene including 2,3-, 2,4-, 2,5- and 2,6-pyridylene, triazinylene including 1,3,5-triazinylene, triazolylene including 1,2,4- and 1,2,3-triazolylene or pyrimidylene including 2,4-, 2,5- and 2,6-pyrimidylene groups. The arylene groups of M are preferably divalent monocyclic, bicyclic or tricyclic groups, including, but not limited to, 1,2-, 1,3- and 1,4-phenylene, and naphthylene.

In other embodiments, M is a chain of repeating monomer units, preferably 1–2000 monomer units, more preferably 1–1000, particularly 1–100, most preferably 1–50 or 1–25 or 1–10, including, but not limited to, ethylene oxide, propylene oxide, methacrylamide, or ethylene glycol. Thus, in certain embodiments, M is a polyethylene glycol (PEG), polypropylene glycol (PPG) or acrylate chain. In particular embodiments, M is a diethyleneglycol, triethyleneglycol or tetraethyleneglycol moiety.

In other embodiments, M contains a cleavable linkage, including, but not limited to, a disulfide, an ester, an enzyme specific peptide, a photocleavable linkage, such as nitroaromatic group, or an acid labile group. Monomers of formula (I) and modified oligonucletides of formula (II) containing such M groups have applications in capture assay methods where the analyte is captured by the modified oligonucleotide, the conjugate isolated, and the M group cleaved to provide an isolated analyte. See, e.g., Niemeyer et al. (1994) *Nucl. Acids Res.* 22(25):5530–5539.

X is preferably —$C(O)R^{30}$, —Y—$N(R^{31})$—$Y^1$—$N(R^{32})$—$Y^2$ or —O—$N(R^{30})$—$Y^2$; where $R^{30}$, $R^{31}$ and $R^{32}$ are each independently hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl or cycloalkyl; Y and $Y^1$ are selected as in (i) or (ii) as follows:

(i) Y is a direct link, and $Y^1$ is a direct link, $C(O)N(R^{35})$, $N(R^{35})C(O)N(R^{36})$, $C(S)N(R^{35})$, $N(R^{35})C(S)N(R^{36})$ or $C(O)N(R^{35})N(R^{36})C(O)N(R^{37})$; or (ii) Y is C(O) or OC(O), and $y^1$ is a direct link;

where $R^{35}$, $R^{36}$ and $R^{37}$ are each independently selected from among hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl and cylcoalkyl; and $Y^2$ is a salt of the hydrazino or oxyamino group, including but not limited to, mineral acid salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group (see, e.g., Greene et al. (1999) *Protective Groups in Organic Synthesis* (3rd Ed.) (J. Wiley Sons, Inc.));

where $R^{30}$, $R^{31}$, $R^{32}$, $R^{35}$, $R^{36}$, $R^{37}$ and $Y^2$ are unsubsituted or substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In certain embodiments herein, $Y^2$ is selected from any amino or hydrazino protecting group, preferably monomethoxytrityl (MMT), 9-fluorenylmethoxycarbonyl (FMOC), acetyl, benzoyl, or a hydrazone or oxime that is cleaved under mild acidic conditions (e.g., 100 mM acetate, pH 4.5–5.5) including, but not limited to, a hydrazone or oxime formed from a lower aliphatic aldehyde or ketone, preferably from acetone, cyclohexanone, propanal or 2-butanone. In other embodiments, particularly when X is a protected oxyamino group, the protecting group is a phthalimidyl group.

The monomers provided herein are added to the growing oligonucleotide chain during enzymatic synthesis. In the case of terminal modification, wherein purification of the final product using a lipophilic handle is required, the amino or hydrazino protecting group is MMT, or a similar moiety. The final protected hydrazino or protected oxyamino substituted product is deprotected following high performance liquid chromatography (HPLC) purification.

1. Hydrazino Derivatives

In one preferred embodiment, the monomers for use in the methods provided herein contain a triphosphate group, as defined herein, a sugar group, a nucleobase, and a hydrazino group (see, FIG. 2). Thus, in this embodiment, the compounds of formula (I) have formula (III):

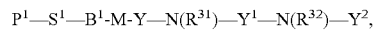

or a derivative thereof, where $P^1$ is a triphosphate group, preferably located at the 5' position of $S^1$;

M is a divalent group having any combination, preferably 1–2000, more preferably 1–1000, particularly 1–100, most preferably 1–50 or 1–25 or 1–10, of the following groups, which can be combined in any order: arylene, heteroarylene, cycloalkylene, $C(R^1)_2$, —$C(R^1)$=$C(R^1)$—, >C=$C(R^2)(R^3)$, >$C(R^2)(R^3)$, —C≡C—, O, $S(A)_a$, $P(D)_b(R^1)$, $P(D)_b(ER^1)$, $N(R^1)$, >$N^+(R^2)(R^3)$ and C(E); where a is 0, 1 or 2;

b is 0, 1, 2 or 3; A is O or NR¹; D is S or O; and E is S, O or NR¹; each R¹ is a monovalent group independently selected from hydrogen and M¹-R⁴; each M¹ is a divalent group independently having any combination of the following groups, which groups can be combined in any order: a direct link, arylene, heteroarylene, cycloalkylene, C(R⁵)₂, —C(R⁵)=C(R⁵)—, >C=C(R²)(R³), >C(R²)(R³), —C≡C—, O, S(A)$_a$, P(D)$_b$(R⁵), P(D)$_b$(ER⁵), N(R⁵), N(COR⁵), >N⁺(R²)(R³) and C(E); where a is 0, 1 or 2; b is 0, 1, 2 or 3; A is O or NR⁵; D is S or O; and E is S, O or NR⁵; R⁴ and R⁵ are each independently selected from among hydrogen, halo, pseudohalo, cyano, azido, nitro, SiR⁶R⁷R⁸, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR⁹R¹⁰; R⁹ and R¹⁰ are each independently selected from hydrogen, alkyl, alkenyl, alkynyl, cycloalkyl, aryl, aralkyl, heteroaryl, heteroaralkyl and heterocyclyl; R² and R³ are selected from (i) or (ii) as follows: (i) R² and R³ are independently selected from among hydrogen, alkyl, alkenyl, alkynyl, cycloalkyl, aryl and heteroaryl; or (ii) R² and R³ together form alkylene, alkenylene or cycloalkylene; R⁶, R⁷ and R⁸ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR⁹R¹⁰;

Y and Y¹ are selected as in (i) or (ii) as follows:

(i) Y is a direct link, and Y¹ is a direct link, C(O)N(R³⁵), N(R³⁵)C(O)N(R³⁶), C(S)N(R³⁵), N(R³⁵)C(S)N(R³⁶) or C(O)N(R³⁵)N(R³⁶)C(O)N(R³⁷); or (ii) Y is C(O) or OC(O), and Y¹ is a direct link;

where R³⁵, R³⁶ and R³⁷ are each independently selected from among hydrogen, alkyl, alkenyl, alkynyl, aryl, heteroaryl, aralkyl, aralkenyl, aralkynyl, heteroaralkyl, heteroaralkenyl, heteroaralkynyl; heterocyclyl and cylcoalkyl;

Y² is a salt of the hydrazino group, including but not limited to, mineral acid salts, such as but not limited to hydrochlorides and sulfates, and salts of organic acids, such as but not limited to acetates, lactates, malates, tartrates, citrates, ascorbates, succinates, butyrates, valerates and fumarates, or any amino or hydrazino protecting group, preferably an amino or hydrazino protecting group useful in the synthesis of oligonucleotides, more preferably monomethoxytrityl (MMT), dimethoxytrityl (DMT), 9-fluorenylmethoxycarbonyl (FMOC), acetyl, trifluoroacetyl (TFA), benzoyl, or a hydrazone that is cleaved under mild acidic conditions (e.g., 100 mM acetate, pH 4.5–5.5) including, but not limited to, a hydrazone formed from a lower aliphatic aldehyde or ketone, preferably from acetone, cyclohexanone, propanal or 2-butanone; and R³¹ and R³² are each independently hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl or cycloalkyl;

where R¹, R², R³, R⁴, R⁵, R⁶, R⁷, R⁸, R⁹, R¹⁰, R³², R³⁵, R³⁶, R³⁷ and Y² are unsubstituted or substituted with one or more substituents each independently selected from Z, as defined above.

In preferred-embodiments, R³¹, R³², R³⁵, R³⁶ and R³⁷ are hydrogen or lower alkyl, more preferably hydrogen. In these embodiments, the compounds of formula (III) have formula (IV):

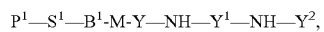

or a derivative thereof, where Y and Y¹ are selected from (i) or (ii) as follows:

(i) Y is a direct link, and Y¹ is a direct link, C(O)NH, NHC(O)NH, C(S)NH, NHC(S)NH or C(O)NHNHC(O)NH; or (ii) Y is C(O) or OC(O), and Y¹ is a direct link;

and P¹, S¹, B¹, M and Y² are selected as above.

In a preferred embodiment, the compounds for use in the methods provided herein are of formula (IV) where M has 1–50, preferably 1–25, more preferably 1–10 of the following groups, which can be combined in any order: arylene, heteroarylene, C(R¹)₂, —C(R¹)=C(R¹)—, —C≡C—, O, S(A)$_a$, N(R¹), N(COR¹) and C(E); where a is 0, 1 or 2; A is O or NR¹; and E is S, O or NR¹; where R¹ is selected as above. In more preferred embodiments, M has 1–10 of the following groups, which can be combined in any order: heteroarylene, C(R¹)₂, —C≡C—, N(R¹) and C(E); where E is S, O or NR¹; where R¹ is selected as above. R¹ is preferably hydrogen; and E is preferably oxygen.

In certain embodiments herein, the group attached to Y is a heteroarylene group, preferably a nitrogen-containing heteroarylene group, preferably a pyrrolylene including 2,3-, 2,4- and 2,5-pyrrolylene, pyridylene including 2,3-, 2,4-, 2,5- and 2,6-pyridylene, triazinylene including 1,3,5-triazinylene, triazolylene including 1,2,4- and 1,2,3-triazolylene or pyrimidylene including 2,4-, 2,5- and 2,6-pyrimidylene group, more preferably a pyridylene group, most preferably a 2,5-pyridylene group. Thus, in these more preferred embodiments, M includes 2,5-pyridylene attached to Y, preferably Y is at the 2-position of the pyridylene group, and 1–9 of the following groups, which can be combined in any order: CH₂, —C≡C—, NH and C(O).

In more preferred embodiments, M has the formula:

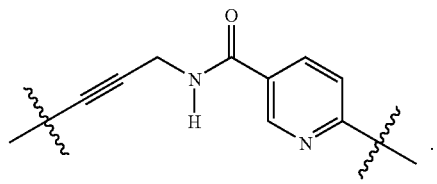

2. Carbonyl Derivatives

In another preferred embodiment, the monomers for use in the methods provided herein contain a triphosphate group, as defined herein, a sugar group, a nucleobase, and a carbonyl group. Thus, in this embodiment, the compounds of formula (I) have formula (V):

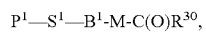

or a derivative thereof, where P¹ is a triphosphate group, preferably located at the 5' position of S¹;

M is a divalent group having any combination, preferably 1–2000, more preferably 1–1000, particularly 1–100, most preferably 1–50 or 1–25 or 1–10, of the following groups, which can be combined in any order: arylene, heteroarylene, cycloalkylene, C(R¹)₂, —C(R¹)=C(R¹)—, >C=C(R²)(R³), >C(R²)(R³), —C≡C—, O, S(A)$_a$, P(D)$_b$(R¹), P(D)$_b$(ER¹), N(R¹), >N⁺(R²)(R³) and C(E); where a is 0, 1 or 2;

b is 0, 1, 2 or 3; A is O or NR¹; D is S or O; and E is S, O or NR¹; each R¹ is a monovalent group independently selected from hydrogen and M¹-R⁴; each M¹ is a divalent group independently having any combination of the following groups, which groups can be combined in any order: a direct link, arylene, heteroarylene, cycloalkylene, C(R⁵)₂, —C(R⁵)=C(R⁵)—, >C=C(R²)(R³), >C(R²)(R³), —C≡C—, O, S(A)$_a$, P(D)$_b$(R⁵), P(D)$_b$(ER⁵), N(R⁵), N(COR⁵), >N⁺(R²)(R³) and C(E); where a is 0, 1 or 2; b is 0, 1, 2 or 3; A is O or NR⁵; D is S or O; and E is S, O or NR⁵; R⁴ and R⁵ are each independently selected from among hydrogen, halo, pseudohalo, cyano, azido, nitro, SiR⁶R⁷R⁸, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR⁹R¹⁰; R⁹ and R¹⁰ are each independently selected from hydrogen, alkyl, alkenyl, alkynyl, cycloalkyl, aryl, aralkyl, heteroaryl, heteroaralkyl and heterocyclyl; R² and R³ are selected from (i) or (ii) as follows: (i) R² and R³ are independently selected from among hydrogen, alkyl, alkenyl, alkynyl, cycloalkyl, aryl and heteroaryl; or (ii) R² and R³ together form alkylene, alkenylene or cycloalkylene; R⁶, R⁷ and R⁸ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR⁹R¹⁰;

R³⁰ is hydrogen, alkyl, alkenyl, alkynyl, aryl, heteroaryl, aralkyl, aralkenyl, aralkynyl, heteroaralkyl, heteroaralkenyl, heteroaralkynyl, heterocyclyl or cycloalkyl;

where R, R²-R³, R⁴, R⁵, R⁶, R⁷, R⁸, R⁹, R¹⁰ and R³⁰ are unsubstituted or substituted with one or more substituents each independently selected from Z, as defined above.

In preferred embodiments, R³⁰ is hydrogen or lower alkyl, more preferably hydrogen or methyl, most preferably hydrogen. In these embodiments, the compounds of formula (V) have formulae (VI):

P¹—S¹—B¹-M-CHO or P¹—S¹—B¹-M-C(O)Me, or a derivative thereof, where P¹, S¹, B¹ and M are selected as above.

In a preferred embodiment, the compounds for use in the methods provided herein are of formula (VI) where M has 1–50, preferably 1–25, more preferably 1–10 of the following groups, which can be combined in any order: arylene, heteroarylene, C(R¹)₂, —C(R¹)=C(R¹)—, —C≡C—, O, S(A)$_a$, N(R¹), N(COR¹) and C(E); where a is 0, 1 or 2; A is O or NR¹; and E is S, O or NR¹; where R¹ is selected as above. In more preferred embodiments, M has 1–10 of the following groups, which can be combined in any order: arylene, C(R¹)₂, —C≡C—, N(R¹) and C(E); where E is S, O or NR¹; where R¹ is selected as above. R¹ is preferably hydrogen; and E is preferably oxygen. In certain embodiments herein, the group attached to CHO or C(O)Me is a arylene group, preferably a monocyclic arylene group, more preferably phenylene. Thus, in these more preferred embodiments, M includes phenylene attached to CHO or C(O)Me, and 1–9 of the following groups, which can be combined in any order: CH₂, —C≡C—, NH and C(O). In other embodiments herein, M preferably includes 1–10, more preferably 1–6, of the following groups, which can be combined in any order: CH₂, —C≡C—, NH and C(O).

In more preferred embodiments, M has the formulae:

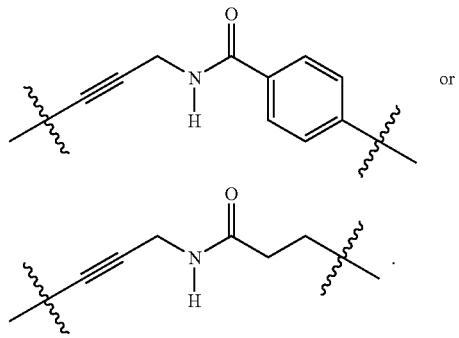

3. Oxyamino Derivatives

In one preferred embodiment, the reagents for use in the methods provided herein contain a triphosphate group, as defined herein, a sugar group, a nucleobase, and an oxyamino group. The oxyamino group is preferably protected as described above. Thus, in this embodiment, the compounds of formula (I) have formula (VII):

P¹—S¹—B¹-M-O—NH—Y², or a derivative thereof, where P¹ is a triphosphate group, preferably located at the 5' position of S¹; S¹ and B¹ are selected as above; and M is a divalent group having any combination, preferably 1–2000, more preferably 1–1000, particularly 1–100, most preferably 1–50 or 1–25 or 1–10, of the following groups, which can be combined in any order: arylene, heteroarylene, cycloalkylene, C(R¹)₂, —C(R¹)=C(R¹)—, >C=C(R²)(R³), >C(R²)(R³), —C≡C—, O, S(A)$_a$, P(D)$_b$(R¹), P(D)$_b$(ER¹), N(R¹), >N⁺(R²)(R³) and C(E); where a is 0, 1 or 2; b is 0, 1, 2 or 3; A is O or NR¹; D is S or O; and E is S, O or NR¹; each R¹ is a monovalent group independently selected from hydrogen and M¹-R⁴; each M¹ is a divalent group independently having any combination of the following groups, which groups can be combined in any order: a direct link, arylene, heteroarylene, cycloalkylene, C(R⁵)₂, —C(R⁵)=C(R⁵)—, >C=C(R²)(R³), >C(R²)(R³), —C≡C—, O, S(A)$_a$, P(D)$_b$(R⁵), P(D)$_b$(ER⁵), N(R⁵), N(COR⁵), >N⁺(R²)(R³) and C(E); where a is 0, 1 or 2; b is 0, 1, 2 or 3; A is O or NR⁵; D is S or O; and E is S, O or NR⁵; R⁴ and R⁵ are each independently selected from among hydrogen, halo, pseudohalo, cyano, azido, nitro, SiR⁶R⁷R⁸, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR⁹R¹⁰; R⁹ and R¹⁰ are each independently selected from hydrogen, alkyl, alkenyl, alkynyl, cycloalkyl, aryl, aralkyl, heteroaryl, heteroaralkyl and heterocyclyl; R² and R³ are selected from (i) or (ii) as follows: (i) R² and R³ are independently selected from among hydrogen, alkyl, alkenyl, alkynyl, cycloalkyl, aryl and heteroaryl; or (ii) R² and R³ together form alkylene, alkenylene or cycloalkylene; R⁶, R⁷ and R⁸ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR⁹R¹⁰;

$Y^2$ is a salt of the oxyamino group, including but not limited to, mineral acid salts, such as but not limited to hydrochlorides and sulfates, and salts of organic acids, such as but not limited to acetates, lactates, malates, tartrates, citrates, ascorbates, succinates, butyrates, valerates and fumarates, or any amino protecting group, preferably an amino protecting group useful in the synthesis of oligonucleotides, more preferably monomethoxytrityl (MMT), dimethoxytrityl (DMT), 9-fluorenylmethoxycarbonyl (FMOC), acetyl, trifluoroacetyl (TFA), benzoyl, or an oxime that is cleaved under mild acidic conditions (e.g., 100 mM acetate, pH 4.5–5.5) including, but not limited to, an oxime formed from a lower aliphatic aldehyde or ketone, preferably from acetone, cyclohexanone, propanal or 2-butanone;

where $R^1$, $R^2$, $R^3$, $R^4$, $R^5$, $R^6$, $R^7$, $R^8$, $R^9$, $R^{10}$ and $Y^2$ are unsubstituted or substituted with one or more substituents each independently selected from Z, as defined above.

In a preferred embodiment, the compounds for use in the methods provided herein are of formula (VII) where M has 1–50, preferably 1–25, more preferably 1–10 of the following groups, which can be combined in any order: arylene, heteroarylene, $C(R^1)_2$, $—C(R^1)=C(R^1)—$, $—C\equiv C—$, O, $S(A)_a$, $N(R^1)$, $N(COR^1)$ and $C(E)$; where a is 0, 1 or 2; A is O or $NR^1$; and E is S, O or $NR^1$; where $R^1$ is selected as above. In more preferred embodiments, M has 1–10 of the following groups, which can be combined in any order: $C(R^1)_2$, $—C\equiv C—$, $N(R^1)$ and $C(E)$; where E is S, O or $NR^1$; where $R^1$ is selected as above. $R^1$ is preferably hydrogen; and E is preferably oxygen. In these more preferred embodiments, M includes 1–10, preferably 1–8, of the following groups, which can be combined in any order: $CH_2$, $—C\equiv C—$, NH and $C(O)$.

In more preferred embodiments, M has the formula:

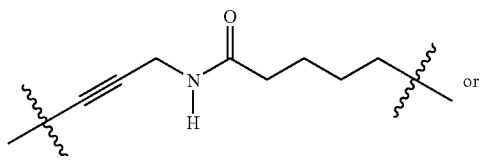

or

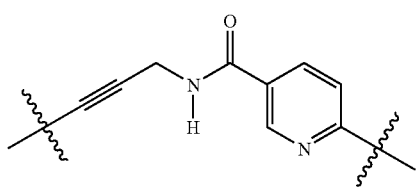

4. Nucleobases $B^1$

The nucleobases $B^1$ of the monomers provided herein are well known to those of skill in the art, and include, but are not limited to, cytosines, uracils, adenines, guanines and thymines, and analogs thereof. including, but not limited to, deaza analogs, such as 7-deazaadenine, 7-deazaguanine and 7-deazahypoxanthine.

Thus, in preferred embodiments, the compounds of formula (I) have the formulae:

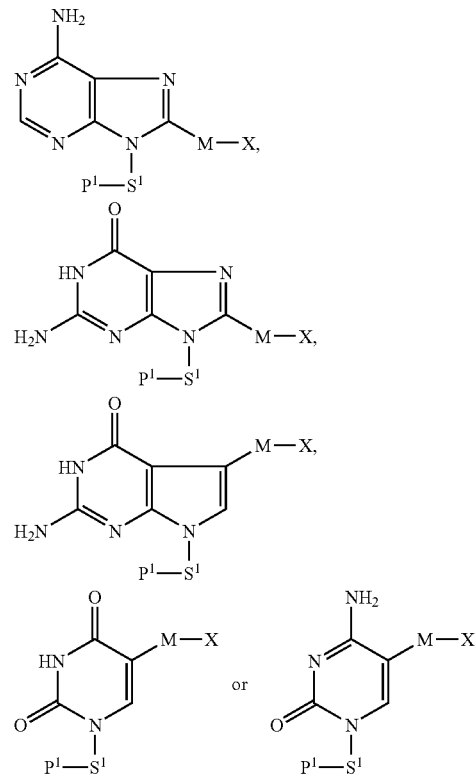

where $P^1$, $S^1$, M and X are selected as above.

5. Sugars $S^1$

The sugars $S^1$ of the monomers provided herein include, but are not limited to, riboses, deoxyriboses including 2'-deoxyriboses, and dideoxyriboses including 2',3'-dideoxyriboses. Other sugars for use herein include arabinoses, including β-D-arabinofuranose, and the riboses 3'-β-D-ribofuranose, 3'-amino-2',3'-dideoxy-β-D-ribofuranose, 2',3'-dideoxy-3'-fluoro-β-D-fibofuranose and 2',3'-dideoxy-2',3'-didehydro-β-D-ribofuranose.

In preferred embodiments, the compounds of formula (I) have the formulae:

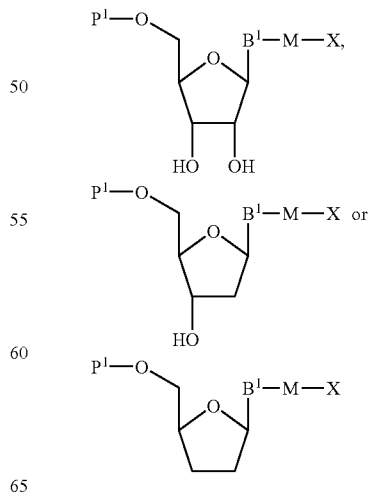

where $P^1$, $B^1$, M and X are selected as above.

6. Preferred Monomers

The presently most preferred compounds of formula (IV) have the structure:

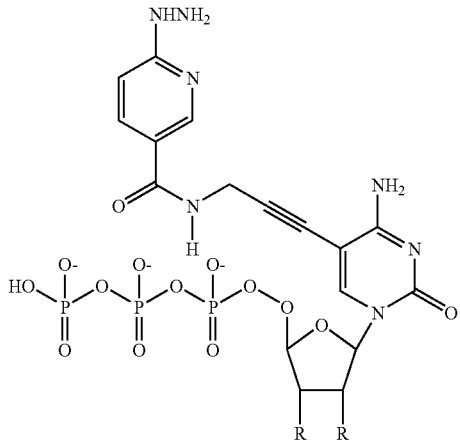

where each R is independently H or OH.

The presently most preferred compounds of formulae (VI) have the structures:

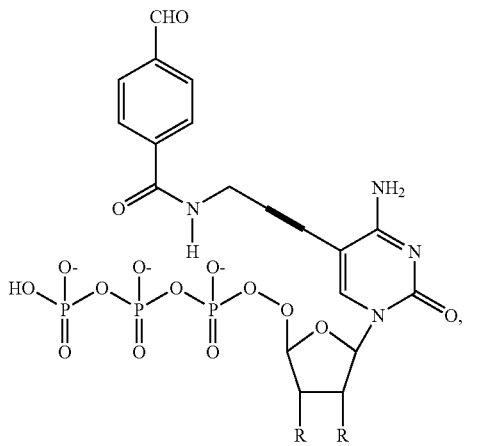

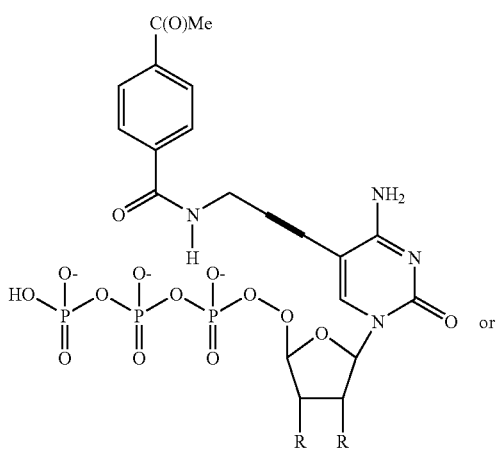

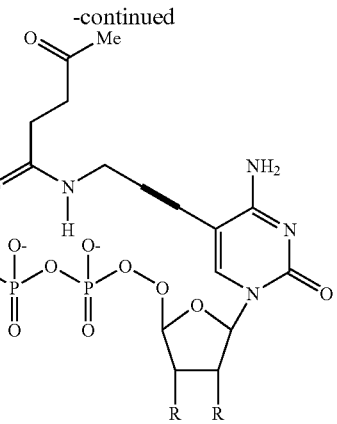

where each R is independently H or OH.

The presently most preferred compounds of formula (VII) have the structures:

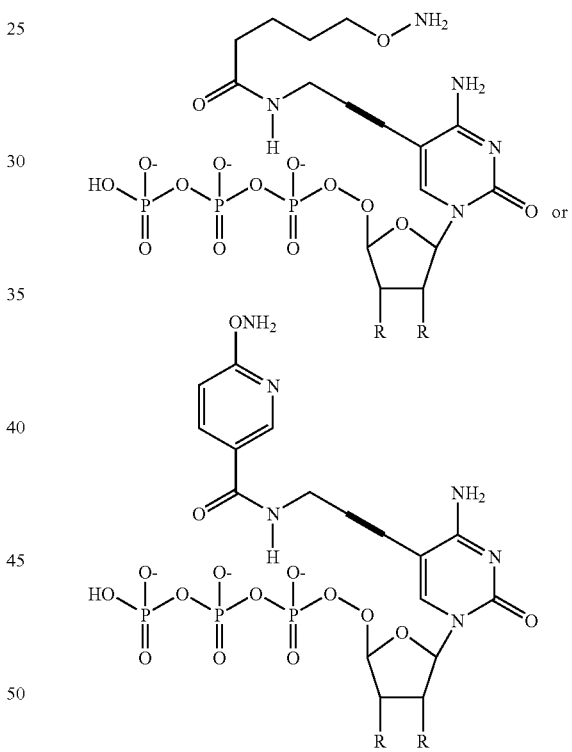

where each R is independently selected from H and OH.

7. Methods of Preparation of the Monomers

Figure 5:
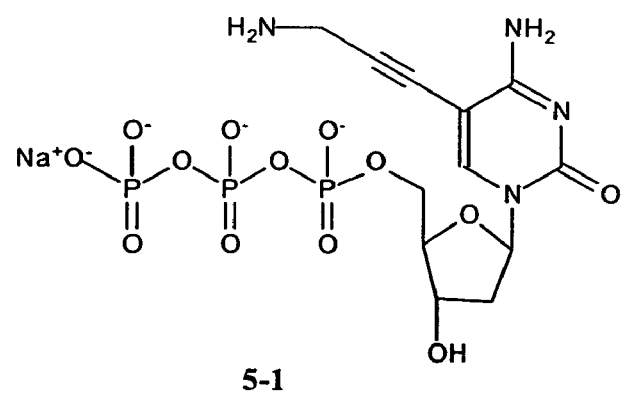
FIG. 5 shows the synthesis of a carbonyl (aldehyde) triphosphate monomer provided herein.
Figure 5:
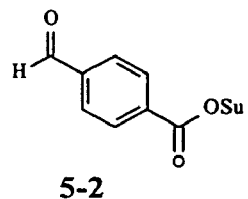
Figure 5:
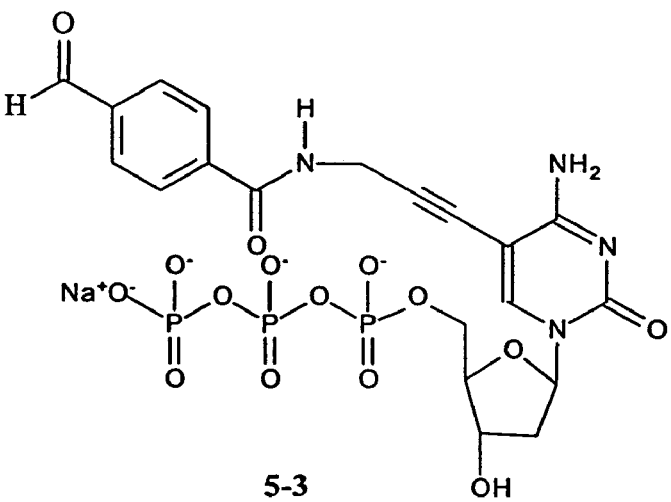

Methods of preparation of the monomers are provided. The methods involving the steps of: (i) derivatizing a carboxylic acid selected from an ω-carbonyl, an ω-protected hydrazino, and an ω-protected oxyamino substituted carboxylic acid as the corresponding active ester, including, but not limited to, aryl, heteroaryl, succinimidyl, maleimidyl, phthalimidyl and naphthimidyl, preferably succinimidyl esters, by reacting the carboxylic acid with the appropriate aryl, heteroaryl, succinimidyl, maleimidyl, phthalimidyl or naphthimidyl alcohol, preferably N-hydroxysuccinimide, under dehydrating conditions, including, but not limited to, in the presence of a carbodiimide, such as dicyclohexylcarbodiimide; and (ii) reacting the resulting active ester with an amino substituted nucleoside triphosphate, including but not limited to a 5-amino substituted cytidine triphosphate such as 5-1, as shown in FIG. 5. Preferred ω-carbonyl carboxylic acids include 4-formylbenzoic acid, levulinic acid and 4-carboxyacetophenone. Preferred ω-protected hydrazino carboxylic acids include 6-(N'-dimethoxytrityl)hydrazinonicotinic acid. Preferred ω-protected oxyamino carboxylic acids include 6-(N-dimethoxytrityl)oxyaminonicotinic acid.

B. Modified Oligonucleotides, Immobilized Oligonucleotides and Oligonucleotide Conjugates 1. Modified Oligonucleotides Provided herein are modified oligonucleotides that possess a hydrazino group (see, FIG. 2), an oxyamino group, or a carbonyl group. These modified oligonucleotides are synthesized directly during enzymatic synthesis without the need for post synthetic modification to produce the hydrazino, oxyamino, or carbonyl group. The modified oligonucleotide first components can be immobilized or conjugated through the formation of covalent hydrazone or oxime bonds. Such hydrazone or oxime bonds can be formed by reaction of the hydrazino, oxyamino or carbonyl modified oligonucleotide first components with appropriately derivatized solid surfaces, as described herein; or second components, including, but not limited to, biopolymers as defined herein, polymers including, but not limited to, polyamines, polyamides, polyethers and polyethylene glycols, and other compounds of interest herein for use in assays, kits, diagnostic arrays, and the like, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that are modified to possess a hydrazino, oxyamino or carbonyl group that is complementary to the carbonyl, oxyamino or hydrazino group of the oligonucleotide of formula (II) for formation of hydrazone or oxime linkage. Dendrimeric compounds that possess a plurality of detectable groups, including, but not limited to, reporter molecules, fluorophores, chromophores, fluorophore precursors and chromophore precursors are also contemplated herein as second components. Fluorophore precursors and chromophore precursors are compounds that react with the hydrazino, oxyamino or carbonyl group of the modified oligonucleotide to form a fluorogenic or chromogenic group for analysis. Fluorophore precursors and chromophore precursors are well known to those of skill in the art, and include, but are not limited to, 3-(4-carboxybenzoyl)quinoline-2-carboxaldehyde (CBQCA) and 3-(2-furoyl)quinoline-2-carboxaldehyde (FQ), sold by Molecular Probes, Inc. (Eugene, Oreg.).

Importantly, the reaction to form the immobilized oligonucleotide or oligonucleotide conjugate can be performed under aqueous conditions without the need for additional reagents, such as a reducing agent.

The modified oligonucleotides provided herein have formula (II):

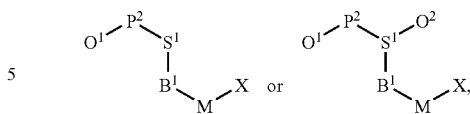

or a derivative thereof, where $O^1$ and $O^2$ are each independently an oligonucleotide or analog thereof, such as a protein nucleic acid (PNA); $P^2$ is a phosphorous linking group resulting from the coupling of a compound of formula (I) with the oligonucleotide or analog thereof, preferably a phosphodiester group; and $S^1$, $B^1$, M and X are selected as above for the hydrazino, oxyamino, and carbonyl monomers.

In certain embodiments, the oligonucleotide analogs of formula (II) are selected with the proviso that if X is CHO, then M is not undecylenecarbonylaminomethylene $(n-C_{11}H_{22}C(O)NHCH_2)$ or $C_{1-20}$alkylene. In other embodiments, the oligonucleotide analogs are of formula (II) where X is not an oxyamino or protected oxyamino group. In further embodiments, the oligonucleotide analogs are of formula (II) where X is not a hydrazide (—C(O)—$NHNH_2$) group. In particular embodiments, the oligonucleotide analogs of formula (II) are selected with the proviso that if X is —$NHNH_2$, then M is not —$CH(CH_2OH)(CH_2)_6NHCO$-5-pyrid-2-ylene. In other embodiments, the oligonucleotide analogs of formula (II) are selected with the proviso that $P^2$ is not a phosphoramidate group.

Thus, in more preferred embodiments, the modified oligonucleotides have formulae:

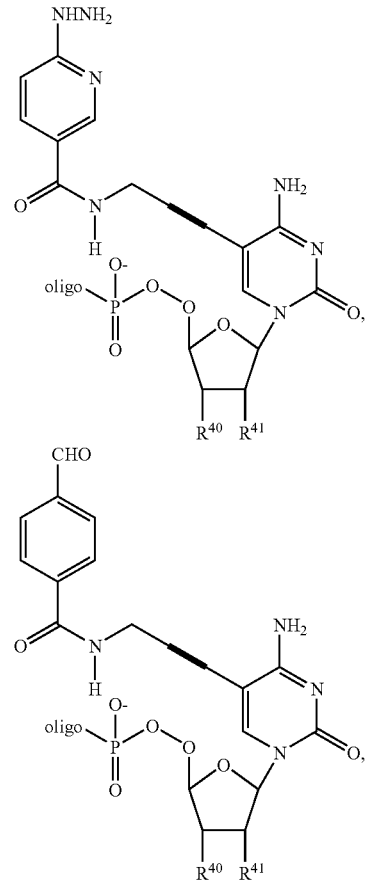

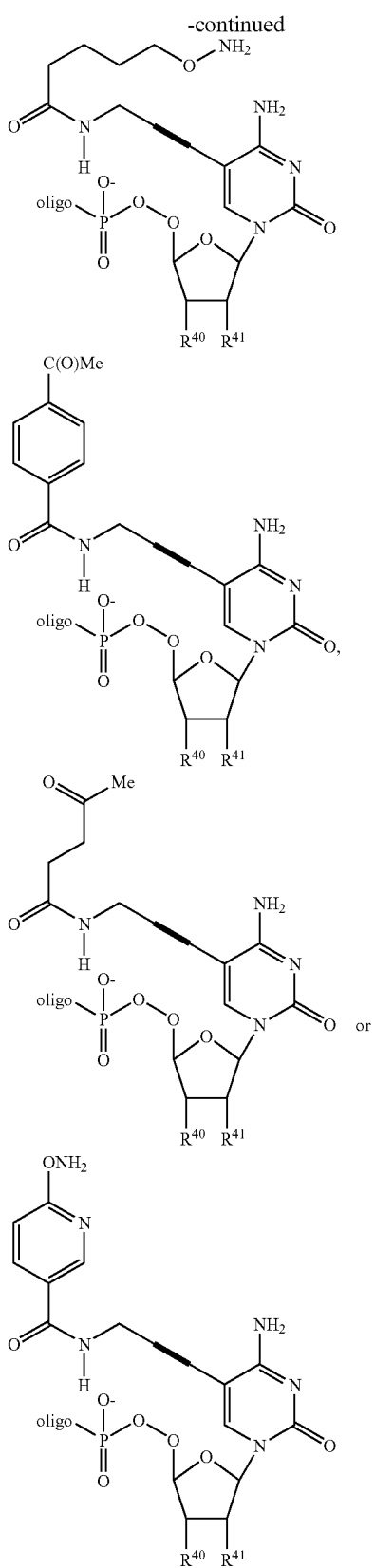

where R⁴⁰ is selected from an oligonucleotide, OH and H; and R⁴¹ is selected from OH and H.

Methods of synthesis of the modified oligonucleotides are also provided. The methods involving the step of contacting a composition having at least one nucleoside triphosphate provided herein with an enzyme for oligonucleotide synthesis under conditions where oligonucleotide synthesis occurs. Preferred enzymes include reverse trascriptases, including, but not limited to, AMV reverse transcriptase, MMLV reverse transcriptase and superscript reverse transcriptase, and polymerases, including, but not limited to, Taq polymerase, DNA plymerase, Klenow fragment and T4 DNA polymerase.

The modified oligonucleotides provided herein are also useful in studying how a normal cell differs from its diseased state. Current gen expression studies require the determination of the expression of any new genes as well as the difference in expression of genes in the two cell states. To this end, RNA from the two cell populations are isolated and cDNA libraries are prepared using reverse transcriptase enzymes and fluorescently labeled triphosphates such as Cy3 and Cy5 triphosphates. It is recognized that the stability and kinetics of incorporation of the labeled triphoshpates are not identical. The modified triphosphates provided herein may be used in both applications. This is advantageous over current methodologies, e.g., amino substituted nucleoside triphosphates (Clonetech) labeled with succinimidyl fluorophores, due to the inherent instability of the succinimidyl esters and the low concentration of amino groups incorporated in the cDNA product.

2. Immobilized Oligonucleotides

Oligonucleotides immobilized through a hydrazone or oxime linkage to a solid surface are provided. The oligonucleotides are or formula (II), and are modified with a hydrazino, oxyamino, or carbonyl moiety. Reaction of the modified oligonucleotide with an appropriately functionalized solid surface provides an immobilized oligonucleotide for use in preparation of microarrays, diagnostic probe assays, DNA amplification by solid phase polymerase chain reactions (PCR), molecular computing (see, e.g., Adleman (1994) Science 266:1021–1024; Kari (1997) Mathematical Intelligencer 19:9–22; Frutos et al. (1997) Nucleic Acids Res. 25:4748; Smith et al. (1998) J. Comp. Biol. 5:255; Liu et al. (1998) J. Comp. Biol. 5:267; Frutos et al. (1998) J. Am. Chem. Soc. 120:10277; Wang et al. (1999) Biosystems 52:189–191; Liu et al. (1999) Biosystems 52:25–33; Liu et al. (2000) Nature 403:175–179; European Patent Application Publication No. EP 0 772 135; Reed et al. (June 2000) Scientific American:86–93), molecular addressing (Niemeyer et al. (1994) Nucl. Acids Res. 22(25):5530–5539), DNA sequencing by mass spectrometry (see, e.g., U.S. Pat. Nos. 6,074,823 and 5,547,835) and in studying the molecular electronics of DNA (see, e.g., U.S. Pat. Nos. 6,071,699, 6,066,448, 5,952,172 and 5,824,473).

Importantly, the reaction to form the immobilized oligonucleotide can be performed under aqueous conditions without the need for additional reagents, such as a reducing reagent.

The modified solid surfaces are prepared on a variety of supports, as described herein. Appropriately modified solid surfaces can be prepared by the methods provided herein and possess carbonyl, oxyamino, or hydrazino groups complementary to the modified oligonucleotide. Reaction of the modified oligonucleotide with the modified solid surface results in covalent attachment of the oligonucleotide to the solid surface through a hydrazone or oxime linkage.

In embodiments where X of the modified oligonucleotide is a hydrazino or oxyamino group, the solid surface can be modified to possess an epoxide, α-bromocarbonyl, maleimide, maleic anhydride, isothiocyanate or isocyanate group. Such solid surfaces can be prepared by methods provided herein or other methods well known to those of skill in the art. For example, reaction of pentafluorophenyl 4-isothiocyanatobenzoate with an amino or hydroxy solid surface results in formation of an isothiocyanato modified solid surface. Some of these surfaces are commercially available from, e.g., Pierce (Rockford, Ill.), SINTEF Applied Chemistry (Trondheim, Norway), Rapp Polymere Gmbh (Tubingen, Germany), and Dyno Particles AS (Trondheim, Norway). Reaction of the hydrazino or oxyamino group of the modified oligonucleotide with the epoxide, α-bromocarbonyl, maleimide, maleic anhydride, isothiocyanate or isocyanate group of the solid surface results in covalent attachment of the oligonucleotide to the solid surface.

In certain embodiments, particularly where X is an oxyamino group, the immobilized oligonucleotides are selected such that the solid surface is not modified with an aldehyde or epoxide group.

3. Oligonucleotide Conjugates

Oligonucleotide first components conjugated to second components, including, but not limited to, biopolymers as defined herein, polymers including, but not limited to, polyamines, polyamides, polyethers and polyethylene glycols, and other compounds of interest herein for use in assays, kits, diagnostic arrays, and the like, including, but not limited to, intercalators, vitamins, reporter molecules, cholesterols, phospholipids, biotin, phenazine, phenanthridine, anthraquinone, acridine, fluoresceins, rhodamines, coumarins, dyes, antibodies, haptens, antigens, enzymes, and detection reagents including, but not limited to, fluorophores, metals including, but not limited to, gold, metal chelates, chromophores, fluorophore precursors and chromophore precursors, that are modified to possess a hydrazino, oxyamino or carbonyl group that is complementary to the carbonyl, oxyamino or hydrazino group of the modified oligonucleotide of formula (II) for formation of hydrazone or oxime linkages are provided. Dendrimeric compounds that possess a plurality of detectable groups, including, but not limited to, reporter molecules, fluorophores, chromophores, fluorophore precursors and chromophore precursors, are also contemplated herein as second components. Fluorophore precursors and chromophore precursors are compounds that react with the hydrazino, oxyamino or carbonyl group of the modified oligonucleotide to form a fluorogenic or chromogenic group for analysis.

Reaction of a modified oligonucleotide of formula (II) with an appropriately modified second component provides a hydrazone or oxime linked conjugate. Thus, in one embodiment, a hydrazino modified oligonucleotide of formula (II) reacts with a carbonyl containing second component, or a second component modified to possess a carbonyl group, such as an aldehyde or a ketone, to afford the conjugate provided herein. In another embodiment, a carbonyl modified oligonucleotide of formula (II) is reacted with a second component containing a hydrazino group, or modified to contain a hydrazino group, to afford the conjugate provided herein. In other embodiments, the modified oligonucleotide possesses an oxyamino or carbonyl group, and the second component possesses a complementary carbonyl or oxyamino group, or is modified to possess a complementary carbonyl or oxyamino group, to afford an oxime linked conjugate.

Importantly, the reaction to form the oligonucleotide conjugate can be performed under aqueous conditions without the need for additional reagents, such as a reducing agent.

C. Hydrazino, Oxyamino and Carbonyl Modified Surfaces

Provided herein are reagents and methods for modification of solid surfaces and second components for use in the methods provided herein. In particular, the modified solid surfaces and second components are useful for the immobilization of the oligonucleotide first components provided herein, and in the conjugation of such first components, respectively.

It is to be understood that the reagents described below are interchangeable in certain applications. For example, a dihydrazine reagent for modification of oligosaccharides can also be used in the modification of solid surfaces to provide a hydrazino solid surface. Many of the other reagents provided below can be used in the preparation of either modified solid surfaces or in the modification of second components for conjugation with the modified oligonucleotides provided herein.

1. Modified Surfaces

Hydrazino, oxyamino and carbonyl modified surfaces are provided. The surfaces provided herein include, but are not limited to, glasses including glasses including controlled pore glass, plastics including polyethylenes, polycarbonates, polypropylenes, polyamides such as Nylon® and polyacrylamides, and polyvinyldenedifluorides, latexes, rubbers, celluloses including nitrocelluloses and diazatized celluloses, latexes, metals including platinum, nickel, zinc, tin, palladium, steel, gold, silver, aluminum, silicon and copper, silicas, agaroses including Sephadex, dextrans including Sepharose, natural sponges, polystyrenes including polystyrene crosslinked with divinylbenzene, polystyrenes radiation grafted onto perfluorinated polymers such as Teflon (see, e.g., Maeji et al. (1994) *Reactive Polymers* 22:203–212; and Berg et al. (1989) *J. Am. Chem. Soc.* 111:8024–8026), oxides of metals and metalloids such as Pt—PtO, Si—SiO, Au—AuO, $TiO_2$, Cu—CuO, and the like, and compound semiconductors, such as lithium niobate, gallium arsenide and indium-phosphide. Other solid surfaces for use herein are well known to those of skill in the art. See, e.g., U.S. Pat. Nos. 4,507,230, 4,006,117, 5,389,449, 5,556,752, 4,683,202 and 5,744,305; International Patent Application. Publication Nos. WO 00/04382, WO 00/04390 and WO 00/04389; Merrifield (1964) *Biochemistry* 3:1385–1390; Berg et al. (1990) in *Innovation Perspect. Solid Phase Synth. Collect. Pap.*, Int. Symp., 1st, Epton, Roger (Ed), pp. 453–459; Berg et al. (1989) in *Pent., Proc. Eur. Pent. SymD.*, 20th, Jung, G. et al. (Eds), pp. 196–198; Berg et al. (1989) *J. Am. Chem. Soc.* 111:8024–8026; Kent et al. (1979) *Isr. J. Chem.* 17:243–247; Kent et al. (1978) *J. Org. Chem.* 43:2845–2852; Mitchell et al. (1976) *Tetrahedron Lett.* 42:3795–3798; and Hermanson et al. (1992) *Immobilized Affinity Ligand Techniques*, Academic Press, Inc., San Diego.

Synthetic solid surfaces include those made from polymers and co-polymers such as polyvinylalcohols, acrylates and acrylic acids such as polyethylene-co-acrylic acid, polyethylene-co-methacrylic acid, polyethy-lene-co-ethylacrylate, polyethylene-co-methyl acrylate, polypropylene-co-acrylic acid, polypropylene-co-methyl-acrylic acid, polypropylene-co-ethyl-acrylate, polypropylene-co-methyl acrylate, polyethylene-co-vinyl acetate, polypropylene-co-vinyl-acetate, and those containing acid anhydride groups such as polyethylene-co-maleic anhydride, polypropylene-co-maleic anhydride and the like. Liposomes have also been used as solid surfaces for affinity purifications (see, e.g., powers et al. (1989) *Biotechnol. Bioeng.* 33:173).

For example, U.S. Pat. No. 5,403,750, describes the preparation of polyurethane-based polymers. U.S. Pat. No.

4,241,537 describes a plant growth medium containing a hydrophilic polyurethane gel composition prepared from chain-extended polyols; random copolymerization is preferred with up to 50% propylene oxide units so that the prepolymer will be a liquid at room temperature. U.S. Pat. No. 3,939,123 describes lightly crosslinked polyurethane polymers of isocyanate terminated prepolymers comprised of poly(ethyleneoxy) glycols with up to 35% of a poly (propyleneoxy) glycol or a poly(butyleneoxy) glycol. In producing these polymers, an organic polyamine is used as a crosslinking agent. Other solid surfaces and preparation thereof are described in U.S. Pat. Nos. 4,177,038, 4,175,183, 4,439,585, 4,485,227, 4,569,981, 5,092,992, 5,334,640, and 5,328,603.

U.S. Pat. No. 4,162,355 describes a polymer suitable for use in affinity chromatography, which is a polymer of an aminimide and a vinyl compound having at least one pendant halo-methyl group. An amine ligand, which affords sites for binding in affinity chromatography is coupled to the polymer by reaction with a portion of the pendant halo-methyl groups and the remainder of the pendant halo-methyl groups are reacted with an amine containing a pendant hydrophilic group. A method of coating a substrate with this polymer is also described. An exemplary aminimide is 1,1-dimethyl-1-(2-hydroxyoctyl)amine methacrylimide and vinyl compound is a chloromethyl styrene.

U.S. Pat. No. 4,171,412 describes specific matrices based on hydrophilic polymeric gels, preferably of a macroporous character, which carry covalently bonded D-aminoacids or peptides which contain D-aminoacid units. The basic carrier is prepared by copolymerization of hydroxyalkyl esters or hydroxyalkylamides of acrylic and methacrylic acid with crosslinking acrylate or methacrylate comonomers are modified by the reaction with diamines, aminoacids or dicarboxylic acids and the resulting carboxyterminal or aminoterminal groups are condensed with D-analogs of aminoacids or peptides. The peptide containing D-aminoacids also can be synthesized stepwise on the surface of the carrier.

U.S. Pat. No. 4,178,439 describes a cationic ion exchanger and a method for preparation thereof. U.S. Pat. No. 4,180,524 describes chemical syntheses on a silica support.

The solid supports can be identifiable, such as by with electronic tags or bar codes (see, e.g., U.S. Pat. No. 6,025, 129; U.S. Pat. No. 6,017,496; U.S. Pat. No. 5,972,639; U.S. Pat. No. 5,961,923; U.S. Pat. No. 5,925,562; U.S. Pat. No. 5,874,214; U.S. Pat. No. 5,751,629; U.S. Pat. No. 5,741, 462), or chemical tags (see, U.S. Pat. No. 5,432,018; U.S. Pat. No. 5,547,839), addressable arrays and other such addressing methods. Supports with electronic tags include supports with radio-frequency tags, such as IRORI MICRO-KANS® and MICROTUBES® microreactors (see, U.S. Pat. No. 6,025,129; U.S. Pat. No. 6,017,496; U.S. Pat. No. 5,972,639; U.S. Pat. No. 5,961,923; U.S. Pat. No. 5,925,562; U.S. Pat. No. 5,874,214; U.S. Pat. No. 5,751,629; U.S. Pat. No. 5,741,462; International PCT application No. WO98/31732; International PCT application No, WO98/15825; and, see, also U.S. Pat. No. 6,087,186).

The solid surfaces can take the form of beads, capillaries, flat supports such as glass fiber filters, multiwell plates, thin films, membranes, wafers, combs, pins, beads in pits of flat surfaces such as wafers (eq., silicon wafers), with or without filter plates, pellets, disks, continuous surfaces such as a microtiter dish or well, hollow fibers, needles, solid fibers, slides, chips, sheets, containers or meshes. The solid surfaces can be formed in arrays for combinatorial synthesis or analysis, or for formation of a combinatorial library. Other supports for use herein include paper plus coated with a suitable matrix The solid surface is modified to possess a hydrazino, oxyamino, or carbonyl group that is complementary to the hydrazino, oxyamino or carbonyl moiety of the oligonucleotide of formula (II) for formation of a hydrazone or oxime linkage.

The hydrazino or oxyamino modified surfaces are prepared from commercially available solid supports or known supports such as those described above. Reaction of the support with, e.g., 5-succinimidyloxycarbonylpyrid-2yl acetone hydrazone having the formula:

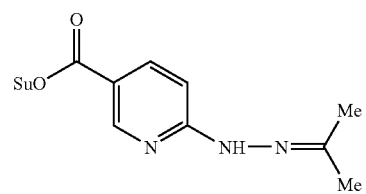

or the corresponding oxyamino compound having the formula:

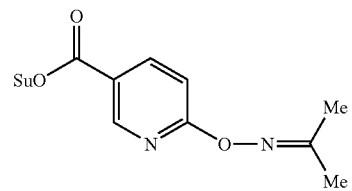

forms a hydrazone or oxime modified solid surface. Alternatively, the hydrazone or oxime succinimidyl esters shown above are reacted with an amino-substituted silane, such as 3-aminopropyltriethoxysilane, to form a silyl hydrazone or oxime. Reaction of the silyl group with a solid surface forms a hydrazone or oxime modified solid surface. Hydrolysis of the hydrazone or oxime group under mild. acidic conditions (e.g., 0.1 M acetate, pH 4.7) affords the hydrazino or oxyamino modified surfaces provided herein. See, co-pending, co-owned U.S. provisional application Serial No. 60/191,186, the disclosure of which is incorporated herein by reference in its entirety.

In one embodiment, hydrazino modified gold surfaces are prepared by reaction with a dihydrazino-dithiol compound of formula X-M-S—S-M-X, where each S is sulfur, each X is independently a protected or unprotected hydrazino group, and each M is independently selected as above. In preferred embodiments, the compound is symmetrical and has the formula (X-M-S—)$_2$. In these embodiments, M preferably has any combination, preferably 1 to 100, more preferably 1 to 50, most preferably 1 to 10, of the following groups: arylene, heteroarylene, C(E), N(R$^1$) and C(R$^1$)$_2$, where E and R$^1$ are selected as above, which groups can be combined in any order. R$^1$ is preferably hydrogen and E is preferably oxygen. In more preferred embodiments, M has 1 to 10 of the following groups: pyridylene, NH, C(O) and CH$_2$, which groups can be combined in any order. M is most preferably derived from cysteamine. Briefly, reaction of cysteamine dimer (i.e., (H$_2$NCH$_2$CH$_2$S)$_2$) with succinimidyl 2-BOC-hydrazino-5-pyridylcarboxylate, followed by deprotection with, e.g., dilute hydrochloric acid, provides the dihydrazino-dithiol:

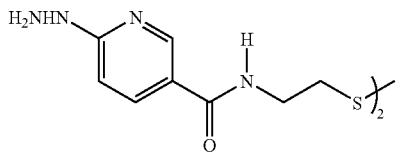

Reaction of this dithiol with a gold surface results in cleavage of the dithiol bond to form a hydrazino modified gold surface (i.e., Au—S—CH$_2$CH$_2$—NHC(O)-pyr-NHNH$_2$).

Carbonyl modified surfaces are prepared from commercially available solid supports such as those described above. Reaction of the support with, e.g., succinimidyl 4-formylbenzoate or 4'-succinimidyloxy-carbonylacetophenone forms a carbonyl, particularly an aldehyde or methyl ketone modified solid surface. Alternatively, succinimidyl 4-formyl benzoate or 4'-succinimidyloxycarbonylacetophenone is reacted with an amino-substituted silane, such as 3-aminopropyltriethoxysilane, to form a silyl aldehyde or ketone. Reaction of the silyl group with a solid surface forms an aldehyde or ketone modified solid surface.

2. Modified Second Components

Hydrazino, oxyamino, and carbonyl modified second components can be prepared by methods provided herein, or by methods well known to those of skill in the art.

a. Modified Oligosaccharides and Proteins

For example, an oligosaccharide can be reacted with cyanogen bromide or 1-cyano-4-dimethylaminopyridinium bromide. (CDAP) to afford a cyano ether of formula R—O—CN. Reaction of this cyano ether with a hydrazino, oxyamino or carbonyl substituted amine, provided herein, affords a hydrazino, oxyamino or carbonyl substituted oligosaccharide, where the hydrazino, oxyamino or carbonyl group is linked to the oligosaccharide through a group of formula —O—C(=NH)—NH—.

In one embodiment, the hydrazino, oxyamino or carbonyl substituted amine provided herein for oligosaccharide modification has the formula:

or a derivative thereof, where M and X are as defined above. In certain embodiments, the compound of formula H$_2$N-M-X is selected where M is not C$_{1-2}$alkyl.

In the above embodiments, the modified oligosaccharide has the formula:

O$^2$—O—C(=NH)—NH-M-X, where O$^2$ is an oligosaccharide; and M and X are as defined above.

Alternatively, oligosaccharides are derivatized as their hydrazino analogs by reaction with CDAP and a dihydrazino compound. The dihydrazino compounds have the formula:

or a derivative thereof, where each X is independently a hydrazino group and M is selected as above. In preferred embodiments, M has any combination, preferably 1 to 100, more preferably 1 to 50, most preferably 1 to 10, of the following groups: arylene, heteroarylene, C(R$^1$)$_2$, N(R$^1$) and C(E), where R$^1$ and E are selected as above, which groups can be combined in any order. In preferred embodiments, R$^1$ is hydrogen and E is oxygen. In more preferred embodiments, M has 1 to 10 of the following groups: heteroarylene, CH$_2$, NH and C(O), which groups can be combined in any order. M most preferably is derived, in these embodiments, from reaction of 1,6-hexanediamine with two equivalents of succinimidyl N'—BOC-6-hydrazinonicotinate. Thus, the reagent of formula X-M-X most preferably has formula:

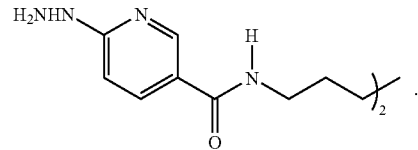

The resulting hydrazino modified oligosaccharide is then conjugated to a carbonyl modified oligonucleotide provided herein. Similarly, di(oxyamino) compounds of formula X-M-X, or a derivative thereof, where X is an oxyamino group and M is selected as above, can be used to generate oxyamino modified oligosaccharides for conjugation with carbonyl modified oligonucleotides.

Polysaccharides or glycoproteins can be oxidized with sodium periodate to yield aldehyde groups directly. These aldehyde groups can be directly labeled with hydrazine modified oligonucleotides as described herein. Lysine moieties on proteins can be modified to incorporate aldehydes using succinimidyl 4-formylbenzoate (Pierce Chemical Co.). These aldehyde containing proteins can be directly conjugated to hydrazine modified oligonucleotides.

Hydrazine groups can also be incorporated on insoluble polysaccharides such as cellulose or agarose using 1-cyano-4-dimethylaminopyridine bromide (CDAP) as described by Lees et al. ((1996) *Vaccine* 14:190 and (2000) *Vaccine* 18:1273) using a dihydrazine molecule (see, e.g., Example 16).

Modified proteins possessing hydrazino or oxyamino groups can be prepared by the methods described in U.S. Pat. Nos. 5,206,370, 5,420,285 and 5,753,520, and European Patent Specification EP 0 384 769 B1, the disclosures of which are incorporated herein by reference in their entirety. These hydrazine modified proteins can be directly conjugated to aldehyde modified oligonucleotides prepared as described herein. Carbonyl modified proteins are prepared by reaction of an aldehyde or ketone substituted succinimidyl ester with nucleophilic groups of the protein, including, but not limited to, the amino side chain of lysine. In certain embodiments, the aldehyde or ketone substituted N-hydroxysuccinic ester is, for example, succinimidyl 4-formyl- or 4-acetylbenzoate. In other embodiments, the protein is reacted with succinimidyl levulinate (succinimidyl 4-oxopentanoate) to provide a ketone substituted protein.

Methods of synthesis of hydrazino, oxyamino, and carbonyl modified oligonucleotides are provided herein.

In other embodiments herein, particularly when the modified oligonucleotide possesses a hydrazino or oxyamino group, the second component can possess an epoxide, α-bromocarbonyl, maleimide, maleic anhydride, isothiocyanate or isocyanate group. Such second components can be prepared by methods provided herein or other methods well known to those of skill in the art. For example, reaction of pentafluorophenyl 4-isothiocyanatobenzoate with an amino or hydroxy group of a second component results in formation of an isothiocyanato modified solid surface. Reaction of the hydrazino or oxyamino group of the modified oligonucleotide with the epoxide, α-bromocarbonyl, maleimide, maleic anhydride, isothiocyanate or isocyanate group of the second component results in covalent attachment of the oligonucleotide to the second component. In these embodiments, the conjugation reaction with a hydrazino modified oligonucleotide can be conducted at a lower pH than for the corresponding amino modified oligonucleotide.

b. Modified Indicators

Modified indicators can be prepared according to the methods provided herein. The modified indicators are conjugated with the modified oligonucleotides of formula (II) to form a hydrazino or oxime linkage. Preferred indicators include, but are not limited to, fluoresceins, rhodamines and cyanine dyes. The modified indicators possess a hydrazino, oxyamino or carbonyl group that is complementary to the carbonyl, oxyamino or hydrazino group of the monomers of formula (I) or the modified oligonucleotides of formula (II).

In one embodiment, the modified indicators have the formula:

F*-M-X, or a derivative thereof, where F* is a fluorescein, a rhodamine or a cyanine dye; X is a protected or unprotected hydrazino group, a protected or unprotected oxyamino group or a carbonyl group; and M is a divalent group having any combination of the following groups, which can be combined in any order: arylene, heteroarylene, cycloalkylene, $C(R^1)_2$, $—C(R^1)=C(R^1)—$, $>C=C(R^2)(R^3)$, $>C(R^2)(R^3)$, $—C\equiv C—$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$; each $R^1$ is a monovalent group independently selected from hydrogen and $M^1$-$R^4$; each $M^1$ is a divalent group independently having any combination of the following groups, which groups can be combined in any order: a direct link, arylene, heteroarylene, cycloalkylene, $C(R^5)_2$, $—C(R^5)=C(R^5)—$, $>C=C(R^2)(R^3)$, $>C(R^2)(R^3)$, $—C\equiv C—$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1, 2 or 3; A is O or $NR^5$; D is S or O; and E is S, O or $NR^5$; $R^4$ and $R^5$ are each independently selected from among hydrogen, halo, pseudohalo, cyano, azido, nitro, $SiR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; $R^9$ and $R^{10}$ are each independently selected from hydrogen, alkyl, alkenyl, alkynyl, cycloalkyl, aryl, aralkyl, heteroaryl, heteroaralkyl and heterocyclyl; $R^2$ and $R^3$ are selected from (i) or (ii) as follows: (i) $R^2$ and $R^3$ are independently selected from among hydrogen, alkyl, alkenyl, alkynyl, cycloalkyl, aryl and heteroaryl; or (ii) $R^2$ and $R^3$ together form alkylene, alkenylene or cycloalkylene; $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and $R^1$ $R^2$, $R^3$, $R^4$, $R^5$, $R^6$, $R^7$, $R^8{}_1$ $R^9$ and $R^{10}$ are unsubstituted or substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In preferred embodiments herein, the modified indicators are those where the fluorescein is 5-aminofluorescein, 6-aminofluorescein, fluorescein 5-isothiocyanate, fluorescein 6-isothiocyanate or fluorescein thiosemicarbazide; the rhodamine is rhodamine 123, rhodamine B, rhodamine B isothiocyanate, rhodamine 6G, rhodamine 110 or ROX having the structure:

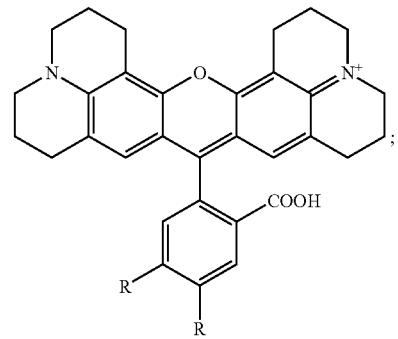

where each R is independently H or COOH; and the cyanine dye is Cy3, benzo-Cy3, dibenzo-Cy3, Cy5, benzo-Cy5, dibenzo-Cy5, Cy7, benzo-Cy7 or dibenzo-Cy7 having the structures:

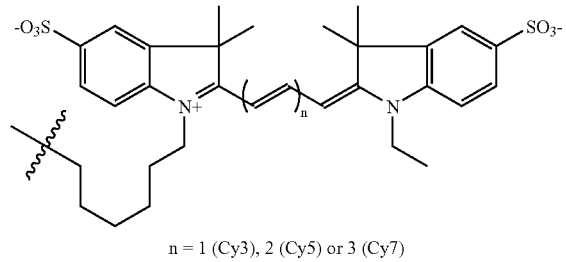

n = 1 (Cy3), 2 (Cy5) or 3 (Cy7)

-continued

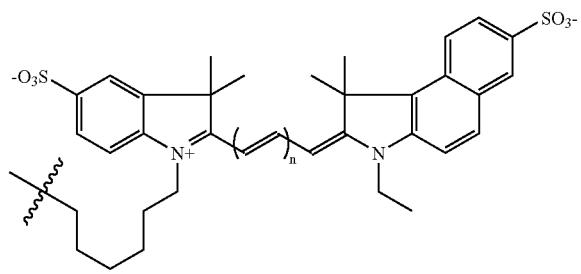

n = 1 (benzo-Cy3), 2 (benzo-Cy5) or 3 (benxo-Cy7)

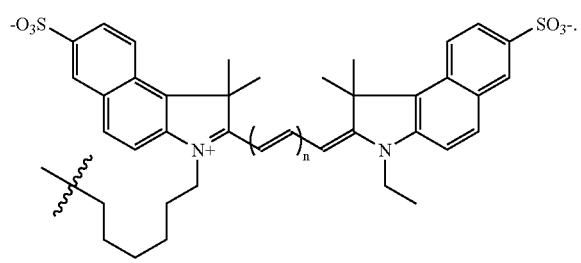

n = 1 (dibenzo-Cy3), 2 (dibenzo-Cy5) or 3 (dibenxo-Cy7)

See, e.g., FIG. 12 and International Patent Application Publication No. WO 99/65993.

In more preferred-embodiments, the modified indicator is chosen from

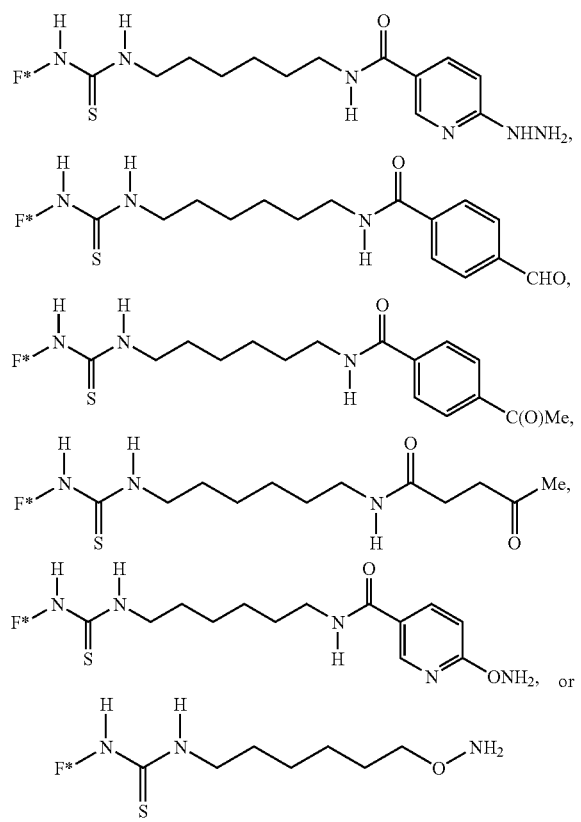

or a derivative thereof, where F* is selected as above.

More preferably, the modified indicators are those where F* is fluorescein, rhodamine, ROX, Cy3 or Cy5. Most preferably, the modified indicators have the formula:

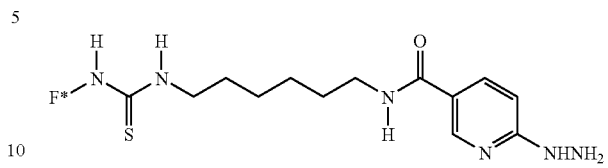

where F* is fluorescein, rhodamine, ROX, Cy3 or Cy5.

D. Methods of Use of Modified Oligonucleotides

The hydrazino, oxyamino, and carbonyl modified oligonucleotides provided herein have application in numerous diagnostic methods. One application is use of the modified oligonucleotides in a DNA probe detection system. See, e.g., U.S. Pat. No. 5,876,938. In such a system, a modified polynucleotide is prepared using random-primed DNA labeling and a hydrazino, oxyamino or carbonyl containing monomer of formula (I) provided herein. It is to be understood that any of the monomers described herein could also be used, as well as alternative methods of polymer formation (e.g., nick translation, solid phase synthesis, and terminal transferase). Following preparation of the hydrazino, oxyamino or carbonyl labeled probe, a blot hybridization can be carried out in which the labeled probe is applied to filter-bound DNA under conditions in which hybridization takes place between the probe and a target polynucleotide. The presence of a target polynucleotide can then be determined using, for example, enzyme-linked detection. Alkaline phosphatase that is linked to a carbonyl, oxyamino or hydrazino, moiety complementary to the hydrazino, oxyamino or carbonyl group of the modified oligonucleotide, will react with the hydrazino, oxyamino or carbonyl portion of the probe. Subsequent treatment with a substrate for alkaline phosphatase which forms a detectable product provides a means by which the presence of the target nucleic acid or polynucleotide can be detected.

Alternatively, the modified oligonucleotides provided herein can be used for affinity purification of a target oligonucleotide. In one embodiment, the probes are prepared as described above and added to a mixture of oligonucleotides containing a target oligonucleotide. Following hybridization, magnetic beads having an attached reactive moiety that is complementary to the hydrazino, oxyamino or carbonyl group of the probe are placed in the mixture and covalent bonding to the hydrazino, oxyamino or carbonyl labeled probe occurs via a hydrazone or oxime linkage. The beads (with attached probe and target) are drawn to a magnetic plate and the remaining materials are washed away.

In other embodiments, the modified oligonucleotides can be used in combination with other purification and labeling methods to provide unique methods of isolating and detecting picogram quantities of target oliognucleotides.

Accordingly, provided herein are methods for detecting the presence of a target nucleic acid in a sample, comprising;

(a) contacting a sample with a modified oligonuicleotide which is substantially complementary to the target nucleic acid under conditions sufficient to hybridize the modified oligonucleotide to the target nucleic acid thereby forming a hybridized complex;

(b) contacting the hybridized complex with a complexing agent which comprises a detectable moiety or an indicator, and a carbonyl, oxyamino or hydrazino moiety that is complementary to the hydrazino, oxyamino or carbonyl group of the modified oligonucleotide; and (c) detecting the presence of the detectable moiety or indicator, thereby detecting the presence of the target nucleic acid.

The hydrazino, oxyamino and carbonyl modified oligonucleotides or formula (II) provided herein are useful in a variety of other methods, including, but not limited to, diagnostic probe assays, DNA amplification by solid phase polymerase chain reactions (PCR), molecular computing (see, e.g., Adleman (1994) *Science* 266:1021–1024; Kari (1997) *Mathematical Intelligencer* 19:9–22; Frutos et al. (1997) *Nucleic Acids Res.* 25:4748; Smith et al. (1998) *J. Comp. Biol.* 5:255; Liu et al. (1998) *J. Comp. Biol.* 5:267; Frutos et al. (1998) *J. Am. Chem. Soc.* 120:10277; Wang et al. (1999) *Biosystems* 52:189–191; Liu et al. (1999) *Biosystems* 52:25–33; Liu et al. (2000) *Nature* 403:175–179; European Patent Application Publication No. EP 0 772 135; Reed et al. (June 2000) *Scientific American:*86–93), molecular addressing (Niemeyer et al. (1994) *Nucl. Acids Res.* 22(25):5530–5539), DNA sequencing by mass spectrometry (see, e.g., U.S. Pat. Nos. 6,074,823 and 5,547,835) and in studying the molecular electronics of DNA (see, e.g., U.S. Pat. Nos. 6,071,699, 6,066,448, 5,952,172 and 5,824,473). In general, the modified oligonucleotide is immobilized as described herein for use in the above methods.

The hydrazino modified oligonucleotides prepared using the reagents of formula (I) are also useful for a variety of additional purposes, including, but not limited to:

(i) direct attachment to surfaces such as carbonyl, i.e., aldehyde or ketone, modified glasses including controlled pore glass, plastics including polyethylene, polypropylene, polyamide and polyvinyidenedifluoride, celluloses including nitrocelluloses, latexes, metals including steel, gold, silver, aluminum, silicon and copper, silicas, agaroses including Sepharose®, Sephadex® and polystyrenes, in the form of beads, capillaries, flat supports such as glass fiber filters, multiwell plates or membranes, wafers, combs, pins (e.g., arrays of pins suitable for combinatorial synthesis or analysis) or beads in pits of flat surfaces such as wafers (e.g., silicon wafers), with or without filter plates; resulting in oligonucleotides attached via a hydrazone bond formed between the hydrazino oligonucleotide and the carbonyl moiety on the surface; and (ii) direct attachment to any biopolymer which has been modified to include a carbonyl moiety using, for example, periodate oxidation of carbohydrates or functionalization of amino moieties using carbonyl modification reagents such as succinimidyl 4-formyl benzoate. See, e.g., Ghosh (European Patent Application Publication No. Ep 0 361 768), the disclosure of which is incorporated herein in its entirety.

In the cases wherein the final hydrazino product is required directly from standard aqueous ammonia deprotection and cleavage from a solid support, the hydrazino protecting group is a labile protecting group, including, but not limited to, FMOC, benzoyl or acetyl, that is removed during deprotection of the other oligonucleotide protecting groups. Thus direct addition of the crude reaction product to a solid surface appropriately modified with a moiety that reacts with the hydrazino function will lead to covalent modification of the surface, and non-hydrazino modified oligonucleotides and other impurities will be washed away.

E. Preparation of the Compounds

1. Monomers

In general, the monomers of formula (I) provided herein can be prepared by methods well known to those of skill in the art, or by modification of those methods using techniques known to those of skill in the art.

For example, monomers of formula (I) where X is a carbonyl group, particularly an aldehyde or ketone group, can be prepared starting from formyl- or keto-substituted carboxylic acids and carboxylic acid derivatives. Many such formyl- or keto-substituted carboxylic acids and carboxylic acid derivatives, including 4-formylbenzoic acid and 4'-carboxyacetophenone are commercially available (see, e.g., Aldrich Chemical Co., Milwaukee, Wis.). Reaction of the succinimidyl ester or other activated ester of these carboxylic acids, prepared, e.g., from the carboxylic acid, N-hydroxysuccinimide and dicyclohexylcarbodiimide, with, e.g., an amino or hydroxy substituted nucleoside triphosphate provides the desired carbonyl substituted nucleoside triphosphate (see, e.g., FIG. 5).

In another example, the monomers of formula (I) where X is a hydrazino group or oxyamino group are prepared starting from hydrazino-or oxyamino-substituted carboxylic acids and carboxylic acid derivatives. Such hydrazino or oxyamino compounds are prepared by reaction of the corresponding halocarboxylic acid with, e.g., hydrazine, hydroxylamine, or derivatives thereof. Semicarbazides and thiosemicarbazides are prepared by reaction of hydrazine with the corresponding isocyanates and isothiocyanates. Carbazides and thiocarbazides can be prepared by reaction of a hydrazine derivative with phosgene or thiophosgene, or an equivalent thereof, and hydrazine. Hydrazides are prepared by reaction of an activated carboxylic acid with hydrazine. A carbonic acid dihydrazine, is prepared by reaction of an isocyanate with carbonic acid dihydrazide. A hydrazine carboxylate can be prepared by reaction of an alcohol with phosgene and hydrazine.

The resulting hydrazino or oxyamino carboxylic acid is then protected. The protecting group is a salt or is any amine or hydrazine protecting group known to those of skill in the art.

Figure 7:
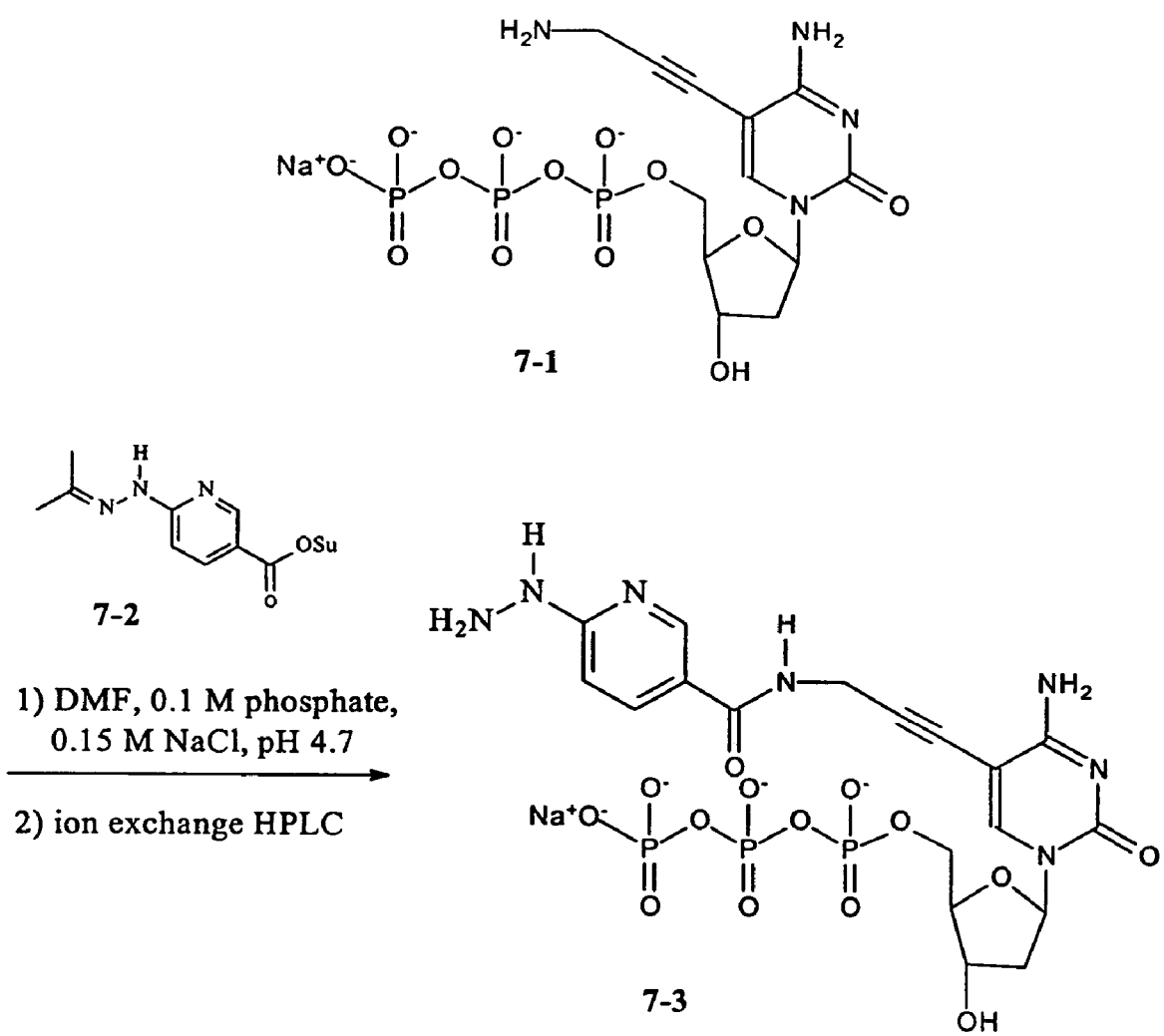
FIG. 7 illustrates the synthesis of a hydrazino triphosphate monomer provided herein.
Figure 8:
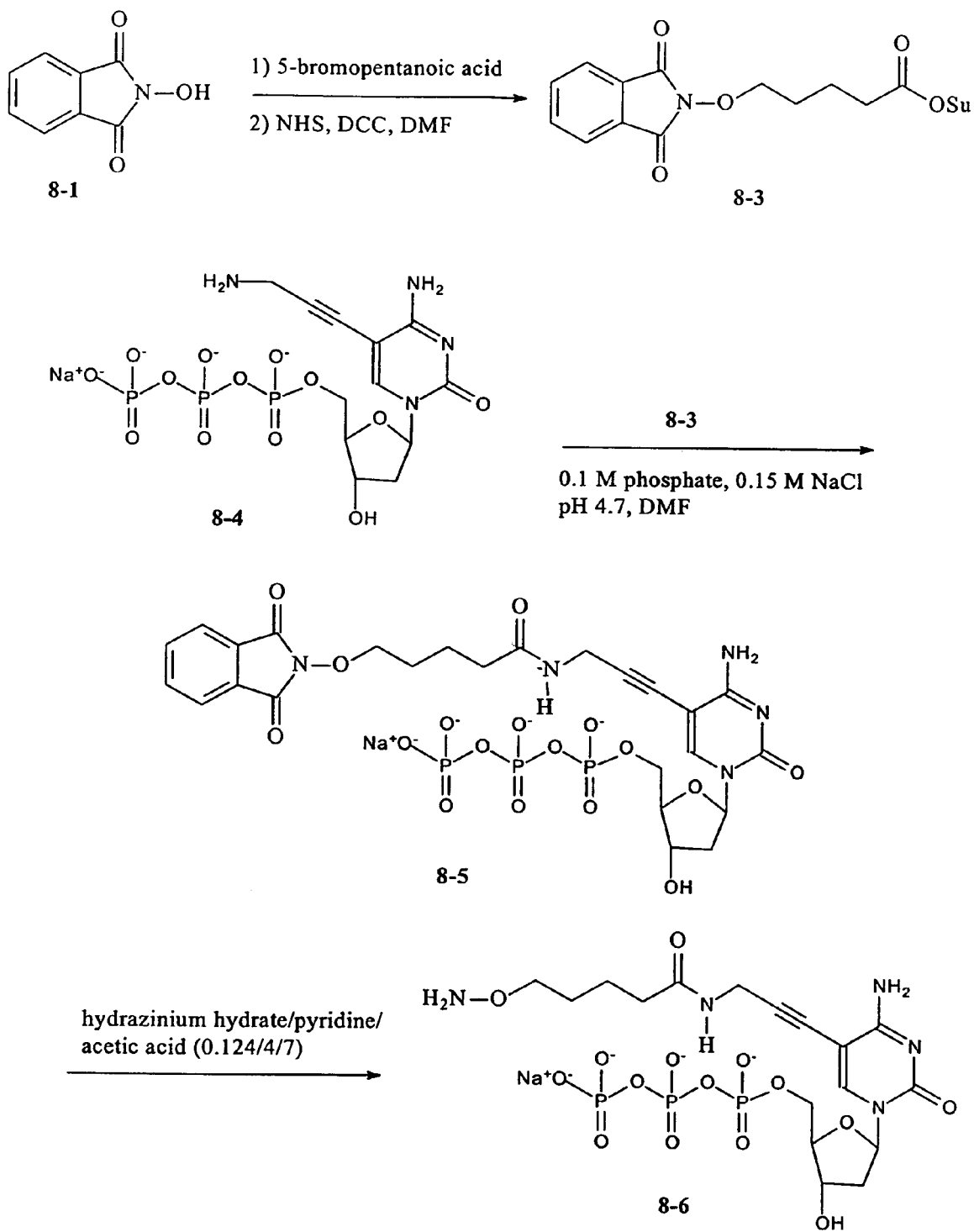
FIG. 8 illustrates the synthesis of an-oxyamino triphosphate monomer provided herein.
Figure 9:
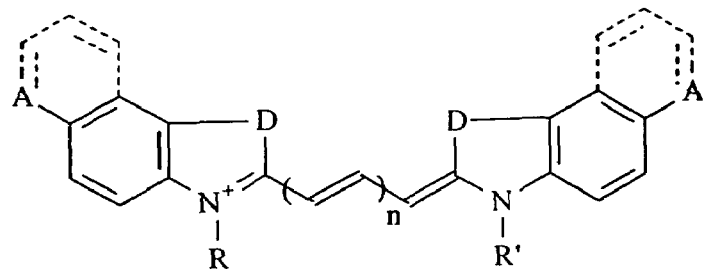
FIG. 9 illustrates the modified fluorescent groups F* provided herein.
Figure 9:
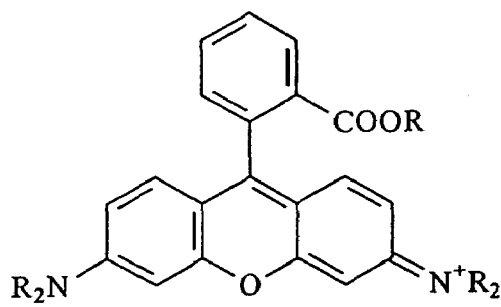
Figure 9:
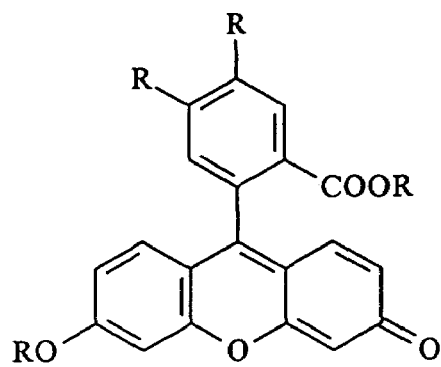

Reaction of the succinimidyl ester or other activated ester of protected hydrazino or protected oxyamino carboxylic acids, prepared, e.g., from the carboxylic acid, N-hydroxysuccinimide and dicyclohexylcarbodiimide, with, e.g., an amino or hydroxy substituted nucleoside triphosphate provides, after deprotection, the desired hydrazino or oxyamino substituted nucleoside triphosphate (see, e.g., FIGS. 7 and 8).

2. Modified Oligonucleotides

The hydrazino, oxyamino or carbonyl-modified oligonucleotides provided herein can be synthesized in solid phase or in solution, using the above hydrazino, oxyamino or carbonyl-modified monomers and other nucleoside bases. In some embodiments, the hydrazino, oxyamino or carbonyl-containing oligonucleotides are prepared using enzyme-based methodology such as PCR, random prime labeling, tailing or nick translation.

The synthesis of modified polynucleotides containing a modified monomer described above can also be achieved by enzyme-based methods. Pyrimidine, purine and deazapurine, preferably cytosine, uracil, adenine, guanine and thymine, more preferably cytosine, nucleoside triphosphates containing a hydrazino, oxyamino or carbonyl moiety linked to the heterocyclic ring can be used as substrates for a wide variety of purified nucleic acid polymerases of both prokaryotic and eukaryotic origin. These include Taq DNA polymerase, DNA polymerase I of *E. coli*, bacteriophage T4 DNA polymerase, DNA polymerases alpha and beta from murine (A-9) and human (HeLa) cells, and the DNA polymerase of Herpes simplex virus. Nick-translation, random prime labeling, and terminal transferase tailing are also useful methods for the incorporation of a modified nucleic acid monomer into an polynucleotide. Nick-translation can -be carried out as described in Rigby, et al. (1977). *J. Mol. Biol.* 113:237–251, incorporated herein by reference. Random prime labeling can be conducted utilizing a modification of the method of Feinberg, et al. (1988) *Anal. Biochem.* 132:6–13 in which a modified monomer is used in place of dTTP. Incorporation can be verified by capture of the probe (or modified oligonucleotide) on DHBHA-Sepharose. Tailing, or terminal transfer can be carried out using the method of Kumar, et al. (1988) *Anal. Biochem.* 169:376–382 in which a modified (boronic acid-containing) monomer is diluted into dTTP. As above, incorporation of the modified monomer can be verified by capture of the probe on DHBHA-Sepharose.

3. Modified indicators

The modified indicators provided herein can be prepared by the following methods, or by other methods known to those of skill in the art. In general, the commercially available (Amersham, BDL) fluorescent compound F* is derivatized as an amine, alcohol or thiol, preferably an amine (see, e.g., FIG. 6). Reaction of this F* derivative with an activated carboxylic acid compound, such as an acyl halide, a mixed anydride, an aryl or heteroaryl ester, a naphthalimidyl ester, or a succinimidyl ester, preferably a succinimidyl ester, that is substituted with a protected hydrazino, protected oxyamino, or carbonyl group followed by deprotection provides the modified indicators of formula F*-M-X provided herein.

Alternatively, the fluorescent compound F* can be derivatized as an activated carboxylic acid compound, such as an acyl halide, a mixed anydride, an aryl or heteroaryl ester, a naphthalimidyl ester, or a succinimidyl ester, preferably a naphthalimidyl ester. Reaction of this F* derivative with an amine, alcohol or carbonyl compound that possesses a protected or unprotected hydrazino, a protected or unprotected oxyamino, or carbonyl moiety affords, following deprotection, the modified indicators provided herein. Certain fluorescent compounds F* that are derivatized as activated carboxylic acids are known to those of skill in the art (see, e.g., International Patent Application Publication No. WO 99/65993, and U.S. Pat. Nos. 4,337,063, 4,404,289, 4,405,711, 5,486,616, 5,569,587, 5,569,766 and 5,627,027).

In another alternative, an amino derivative of a fluorescent compound F* is converted to the corresponding isothiocyanate by reaction with, e.g., thiophosgene or thiocarbonyidiimidazole, and a tertiary amine, such as triethylamine or, diisopropylethylamine. Reaction of this isothiocyanate derivative with an amine possessing a protected hydrazino, protected oxyamino or carbonyl group gives, following deprotection, the hydrazino, oxyamino and carbonyl modified indicators provided herein. Alternatively, reaction of the isothiocyanate derivative with an α,ω-diaminoalkane, such as 1,6-diaminohexane, followed by reaction with a protected hydrazino, protected oxyamino or carbonyl modified succinimidyl ester, as described herein, gives, after deprotection, the hydrazino, oxyamino or carbonyl modified indicators provided herein.

The following examples are included for illustrative purposes only and are not intended to limit the scope of the invention.

EXAMPLE 1

Synthesis of Aldehyde Triphosphate

5-Amino substituted cytidine triphosphate 5-1 was prepared from 2-deoxycytidine as described in U.S. Pat. No. 5,242,796. As shown in FIG. 5, triphosphate 5-1 was dissolved in 0.1 M phosphate, 0.15 M sodium chloride, pH 7.4 and diluted with DMF. A solution of succinimidyl 4-formylbenzoate (5-2; mmol, equiv, Pierce Chemicals, Rockford, Ill.) in DMF was added to the triphosphate. The reaction mixture was incubated at room temperature and the progress of the reaction was followed by C-18 reverse phase HPLC (mobile phase 1:50 mM triethylammbnium acetate, pH 7.4, mobile phase 2: acetonitrile; gradient: 0% 2 to 20% 2 over 20 min, 20% 2 to 50% 2 over 5 min; flow: 2 mL/min). Further reagent was added to drive the reaction to completion.

The product 5-3 was isolated by ion-exchange HPLC using DEAE-Sephadex with a gradient from water (500 mL) to 0.6 M LiCl (500 mL) as the eluting buffer. The compound was desalted by precipitation from acetone/MeOH. $^{31}$P NMR, $^1$H NMR and mass spectral data confirmed the structure of the product.

EXAMPLE 2

A. Synthesis of N-(6-fluoresceinyl)-N'-(6-aminohexyl)-thiourea

Figure 6:
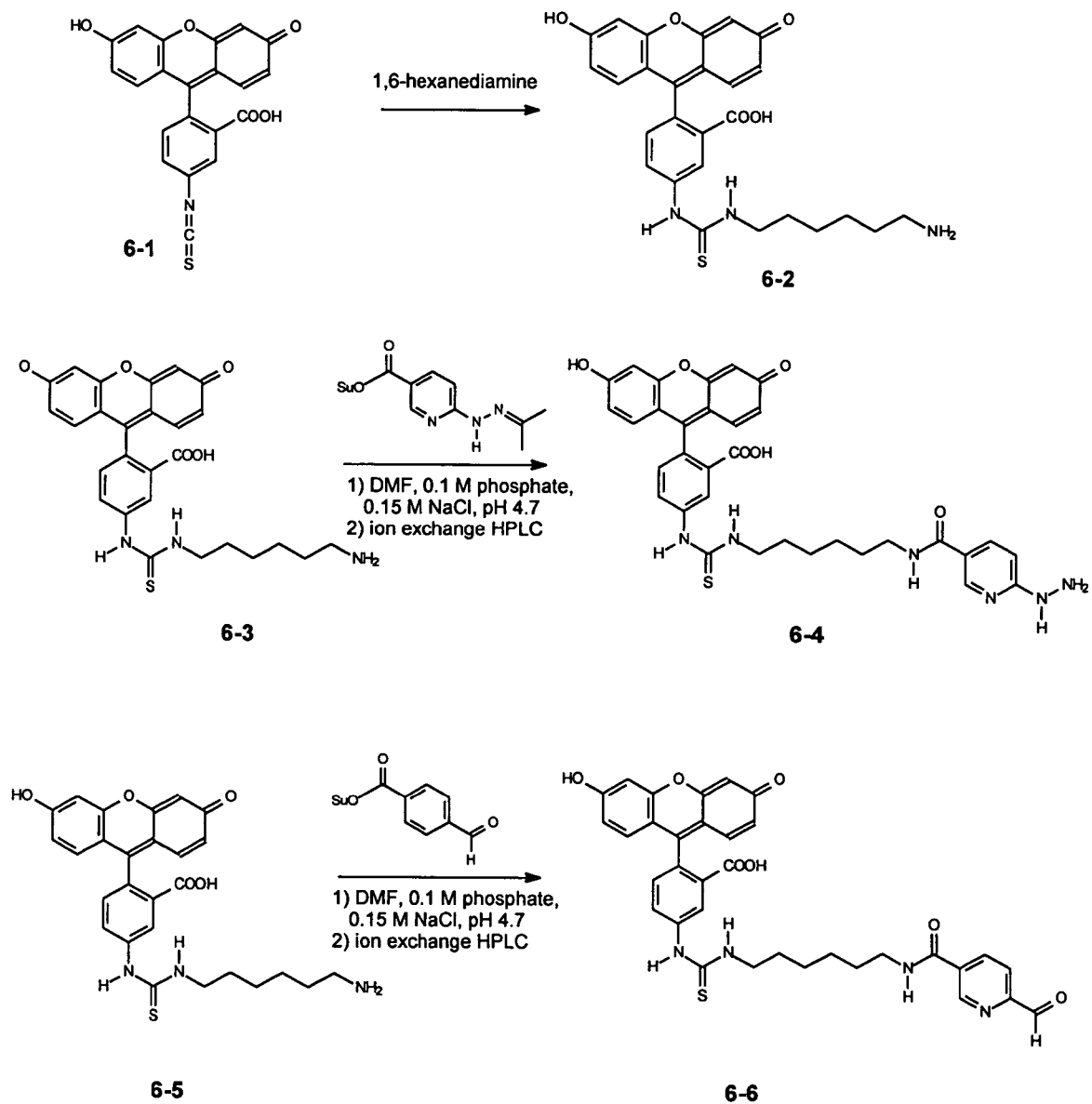
FIG. 6 shows the synthesis of a hydrazino modified fluorescein provided herein.

As shown in FIG. 6, this compound was obtained by dissolving fluorescein isothiocyanate 6-1 (FITC)(1.03 g, 2.64 mmol) in 15 ml of MeOH in a 50 ml oven dried flask. This formed an orange suspension that was allowed to stir for 5 min at room temperature after which 1,6-diaminohexane (1.23 g, 10.56 mmol) was added all at once and the solution instantly went homogeneous. This solution was allowed to stir at room temperature for 48 hr and was covered with aluminum foil after which the reaction was completely evaporated in vacuo. The residue was dissolved in a solution of 1:1:3 EtOAc:MeOH:AcOH (4 ml). This solution was loaded onto a column packed with 61 g of silica. The column had an inner radius of 2 cm. 500 ml of 1:1:2 EtOAc:MeOH:AcOH was pushed through the column by pressure and fractions were collected and analyzed by TLC. The product 6-2 had a $R_f$ of 0.68 and this spot was collected and evaporated to dryness followed by 5×20 ml co-evaporation with MeOH. Yield: 1 g of an orange solid. 75% yield. Mass spec, NMR, and RP-HPLC all indicated pure material.

B. Synthesis of N-(6-fluoresceinyl)-N'-(6-(2-hydrazino-5-pyridylcarbonyl)aminohexyl)-thiourea hydrochloride The product of Example 2.A 6-2 (174 mg, 0.344 mmol) was dissolved in 5 ml of dry DMF and treated with a solution of succinimidyl 2-BOC-hydrazino-5-pyridinecarboxylate (100 mg, 0.344 mmol) in 2 ml of DMF added by syringe all at once at room temperature. The reaction mixture was allowed to stir covered for 24 hr after which the reaction was evaporated to dryness on rota vap. 4 M HCl in dioxane (40 ml) was added. A precipitate instantly formed. After 4 h, the precipitate was filtered and washed with 4×5 ml dioxane to yield, 200 mg of 6–3 as an orange solid. 95% yield. $^1$H NMR and mass spectrometry (calc 641.4; found 641.4) confirmed the structure.

C. Synthesis of N-(6-fluoresceinyl)-N'-(6-(4-formyl-benzoyl)amino-hexyl)-thiourea The product of Example 2.A 6-2 (100 mg, 0.198 mmol) was dissolved in a 1:2 solution of DMF:100 mM phosphate 1 mM NaCl buffer (pH 7.5)(10 ml). Succinmidyl 4-formyl-benzoate (244 mg, 0.990 mmol) in 4 ml of dry DMF was added by syringe all at once. This solution was allowed to stir at room temperature for 48 hr, then was evaporated to dryness on rota-vap. The ensuing residue was treated with 40 ml of dioxane and allowed to sit overnight in the dark to induce precipitation. The precipitate was then filtered off and precipitated one more time with $EtO_2$ to yield 110 g of pure yellow solid 6-4. 84% yield.

PAGE gel of the radiolabeled products demonstrates that reactions that included 10% and 30% aldehyde-dCTP yielded full length product.

EXAMPLE 4

Fluorescent Labeling of Aldehyde Incorporated PCR Product

Determination of incorporation of aldehyde-dCTP was performed by incubation of hydrazino-fluorescein 6-3 with Qiagen purified PCR products (from Example 3) in 0.1 M acetate, pH 5.0 for 2 hours at room temperature. The labeling reaction was terminated by addition of one volume of 0.1 M Tris-HCl, pH 7.5. The sample was purified twice with a Qiagen PCR purification kit and eluted into a final volume of 25 μL in EB buffer provided by Qiagen. Fluorescent signal was assayed by spotting 2 μl of sample onto a microscope slide (Gold Seal, Fisher Scientific) and analysis using a ScanArray Fluorescent Scanner.

EXAMPLE 3

Incorporation of aldehyde triphosphate 5-3 in PCR reaction

| Oligonucleotide | Sequence | Source |
| --- | --- | --- |
| M13Fcomplement5'G | GGT CGT GAC TGG GAA AAC | (SEQ ID NO:1) Trilink |
| M13F | GTT TTC CCA GTC ACG AC | (SEQ ID NO:2) Genosys |
| M13R | AGC CCA TAA CAA TTT CAC ACA GGA | (SEQ ID NO:3) Genosys |
| TF3 | AT GGA AGA ATC TCT CC | (SEQ ID NO:4) Genosys |
| Ferritin283 | GGA ACA TGC TGA AAA CTG | (SEQ ID NO:5) Genosys |
| b-actin300 | TCA CCA ACT GGG ACG ACA TG | (SEQ ID NO:6) Genosys |

Oligonucleotide suppliers: Genosys, Inc (Woodlands, TX); Trilink Bio-technologies (San Diego, CA).

The incorporation of aldehyde-dCTP into PCR generated double stranded DNA was performed using Stoffel Taq Polymerase (Perkin-Elmer) using buffer provided by the manufacturer and 3.5 mM $MgCl_2$. Deoxynucleotides dGTP, dATP and TTP were present at 0.6 mM while primers M13 and M13 R (see sequences above) were used at 1 μM. The DNA template was plasmid 80109 from the IMAGE Consortium collection of human cDNAs. PCR used different amounts of dCTP and aldehyde-dCTP at combined concentration of 0.6 mM. Individual reactions contained 0, 0.6, 0.18 and 0.6 mM aldehyde d-CTP. Syntheses of PCR products from each reaction was determined by radioincorporation of $^{32}P$ into Qiagen purified PCR product. The

EXAMPLE 5

Incorporation of aldehdye-triphosphate by a variety of enzymes using a single-nucleotide extension assay

| Oligonucleotide | Sequence | Source |
| --- | --- | --- |
| M13Fcomplement5'G | GGT CGT GAC TGG GAA AAC | (SEQ ID NO:1) Trilink |
| M13F | GTT TTC CCA GTC ACG AC | (SEQ ID NO:2) Genosys |
| M13R | AGC CCA TAA CAA TTT CAC ACA GGA | (SEQ ID NO:3) Genosys |
| TF3 | AT GGA AGA ATC TCT CC | (SEQ ID NO:4) Genosys |
| Ferritin283 | GGA ACA TGC TGA AAA CTG | (SEQ ID NO:5) Genosys |
| b-actin300 | TCA CCA ACT GGG ACG ACA TG | (SEQ ID NO:6) Genosys |

Oligonucleotide suppliers: Genosys, Inc (Woodlands, TX); Trilink 5 Bio-technologies (San Diego, CA)

$^{32}$P-labeling: Oligonucleotides were radiolabeled with $^{32}$P using gamma $^{32}$P-ATP 3000 Ci/mmol at 10 Ci/mL (ICN, Inc.). The labeling reaction was performed with 20 picomoles Oligonucleotide, 60 uCi gamma 32P ATP, 10 units T4 polynucleotide kinase (Gibco BRL) and 1 µL 10× reaction buffer provided by the manufacturer. The reaction was incubated for 20 minutes at 37° C. $^{32}$P labeled oligonuclotides were purified using a Qiagen nucleotide purification kit and samples ere eluted into 50 µL dH2) and stored at −20° C.

Extension Assay

Oligonucleotides M12F complement 5'G and M13F were combined at a final concentration of 4 µM along with 8.5×106 cpm 32 labeled M13F in a final volume of 16 µL. The mixture was incubated at 80° C. for 3 minutes and allowed to cool to room temperature. Single nucleotide extension assays were performed using a variety of enzymes, i.e., T4 DNA polymerase, Klenow, *E. coli* DNA polymerase I, Stoffel Taq polymerase, Superscript reverse transcriptse, MMLV reverse transcriptase, and AMV reverse transcriptase. Reaction conditions used buffers supplied by the manufacturers. Reactions also contained either dCTP or aldehdye-dCTP. Extension reactions were stopped by freezing at −20° C. Analysis of extension reactions was performed by polyacrylamide gel electrophoresis an a 12.5% polyacrylamide gel containing 8M urea.

EXAMPLE 6

Synthesis of Hydrazine Triphosphate

5-Amino substituted cytidine triphosphate 7-1 was prepared from 2-deoxycytidine as described in U.S. Pat. No. 5,242,796. As shown in FIG. 7, triphosphate 7-1 was dissolved in 0.1 M phosphate, 0.15 M sodium chloride, pH 7.4 and diluted with DMF. A solution of succinimidyl 6-hydrazinonicotinate acetone hydrazone (7-2; 5 equiv, Pierce Chemicals, Rockford, Ill.) in DMF was added to the triphosphate. The reaction mixture was incubated at room temperature and the progress of the reaction was followed by C-18 reverse phase HPLC (mobile phase 1:50 mM triethylammonium acetate, pH 7.4, mobile phase 2: acetonitrile; gradient as in Example 1). Further reagent was added to drive the reaction to completion. The product 7-3 is isolated by ion-exchange HPLC using conditions as described in Example 1.

EXAMPLE 7

Synthesis of Aminooxy Triphosphate

As shown in FIG. 8, a solution of N-hydroxyphthalimide (1 equiv; 8-1; Aldrich Chemical Co., Milwaukee, Wis.) is dissolved in DMF and treated with triethylamine (1 equiv) and 5-bromopentanoic acid (1 equiv.; Aldrich Chemical Co.). The reaction mixture is heated at 50° C. and the progress of the reaction followed by silica gel thin layer chromatography until complete. The solvent is removed under reduced pressure and the residue is partitioned between ethyl acetate and 5% citric acid. The organic phase is washed with brine, dried (magnesium sulfate, filtered and concentrated to the crude product. The product 8-2 is purified by silica gel chromatography.

To a solution of acid 8-2 (1 equiv) in THF is added N-hydroxysuccinimide (1 equiv: Aldrich Chemical Co.) and a solution of dicyclohexyl-carbodiimide (1 equiv; Aldrich Chemical Co.) The reaction mixture is stirred at room temperature for 4 hours and the precipitate that forms (dicyclohexylurea) is removed by filtration. The filtrate is concentrated to dryness and the residue is recrystallized to yield desired succinimidyl ester 8-3.

5-Amino substituted cytidine triphosphate 8-4 (prepared from 2-deoxycytidine according to the procedure of U.S. Pat. No. 5,242,796) is dissolved in 0.1 M phosphate, 0.15 M sodium chloride, pH 7.4 to prepare a 10 mg/mL solution and diluted with an equal volume of DMF. A solution of 8-3 (1 equiv) in DMF is added to the triphosphate solution. The reaction mixture is incubated at room temperature and the progress of the reaction is followed by C-18 reverse phase HPLC (mobile phase 1: 50 mM triethylammonium acetate, pH 7.4, mobile phase 2: acetonitrile; gradient as described in Example 1). Further 8-4 is added to drive the reaction to completion. The product 8-5 is isolated by ion-exchange HPLC. $^{31}$P NMR, $^{1}$H NMR and mass spectral data confirmed the structure of the product.

Phthalimide 8-5 is converted into oxyamino 8-6 by addition of 8-5 to a solution of hydrazinium acetate. The reaction mixture is incubated at room temperature. The purified product is isolated by ion exchange chromatography.

Since modifications will be apparent to those of skill in this art, it is intended that this invention be limited only by the scope of the appended claims.

---

What is claimed is:

1. A compound that has formula (II):

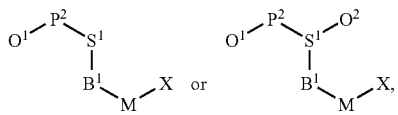

or a derivative thereof, wherein:
- $O^1$ and $O^2$ are each independently an oligonucleotide or an analogs thereof;
- $P^2$ is a phosphodiester group;
- $S^1$ is a ribose, a deoxyribose or a dideoxyribose;
- $B^1$ is a nucleobase;
- X is a protected or unprotected hydrazino group, a protected or unprotected oxyamino group, or a carbonyl derivative; and
- M is a divalent group having any combination of the following groups, which can be combined in any order: arylene, heteroarylene, cycloalkylene, $C(R^1)_2$, $-C(R^1)=C(R^1)-$, $>C=C(R^2)(R^3)$, $>C(R^2)(R^3)$, $-C\equiv C-$, O, $S(A)_a$, $P(D)_b(R^1)$, $P(D)_b(ER^1)$, $N(R^1)$, $>N^+(R^2)(R^3)$ and C(E); where a is 0, 1 or 2; b is 0, 1, 2 or 3; A is O or $NR^1$; D is S or O; and E is S, O or $NR^1$;
- each $R^1$ is a monovalent group independently selected from hydrogen and $M^1\text{-}R^4$;
- each $M^1$ is a divalent group independently having any combination of the following groups, which groups can be combined in any order: a direct link, arylene, heteroarylene, cycloalkylene, $C(R^5)_2$, $-C(R^5)=C(R^5)-$, $>C=C(R^2)(R^3)$, $>C(R^2)(R^3)$, $-C\equiv C-$, O, $S(A)_a$, $P(D)_b(R^5)$, $P(D)_b(ER^5)$, $N(R^5)$, $N(COR^5)$, $>N^+(R^2)(R^3)$ and C(E); where a is 0, 1 or 2; b is 0, 1, 2 or 3; A is O or $NR^5$; D is S or O; and E is S, O or $NR^5$;
- $R^4$ and $R^5$ are each independently selected from the group consisting of hydrogen, halo, pseudohalo, cyano, azido, nitro, $SIR^6R^7R^8$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$;
- $R^9$ and $R^{10}$ are each independently selected from hydrogen, alkyl, alkenyl, alkynyl, cycloalkyl, aryl, aralkyl, heteroaryl, heteroaralkyl and heterocyclyl;
- $R^2$ and $R^3$ are selected from (i) or (ii) as follows:
  (i) $R^2$ and $R^3$ are independently selected from the group consisting of hydrogen, alkyl, alkenyl, alkynyl, cycloalkyl, aryl and heteroaryl; or
  (ii) $R^2$ and $R^3$ together form alkylene, alkenylene or cycloalkylene;
- $R^6$, $R^7$ and $R^8$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^9R^{10}$; and
- $R^1$, $R^2$, $R^3$, $R^4$, $R^5$, $R^6$, $R^7$, $R^8$, $R^9$ and $R^{10}$ are unsubstituted or substituted with one or more substituents each independently selected from Z, wherein Z is selected from alkyl, alkenyl, alkynyl, aryl, cycloalkyl, cycloalkenyl, hydroxy, $S(O)_hR^{20}$, $NR^{20}R^{21}$, $COOR^{20}$, $COR^{20}$, $CONR^{20}R^{21}$, $OC(O)NR^{20}R^{21}$, $N(R^{20})C(O)R^{21}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; h is 0, 1 or 2; and $R^{20}$ and $R^{21}$ are each independently selected from the group consisting of hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

2. The compound of claim 1 that has any of formula:

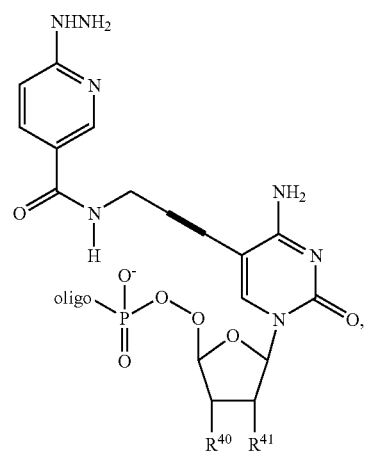

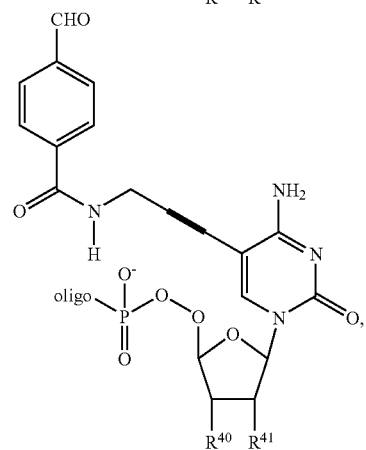

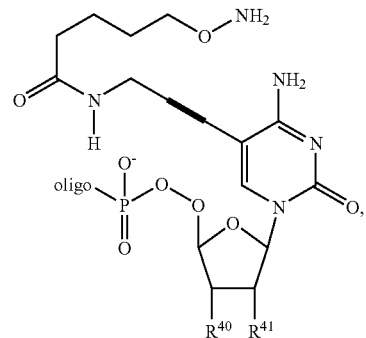

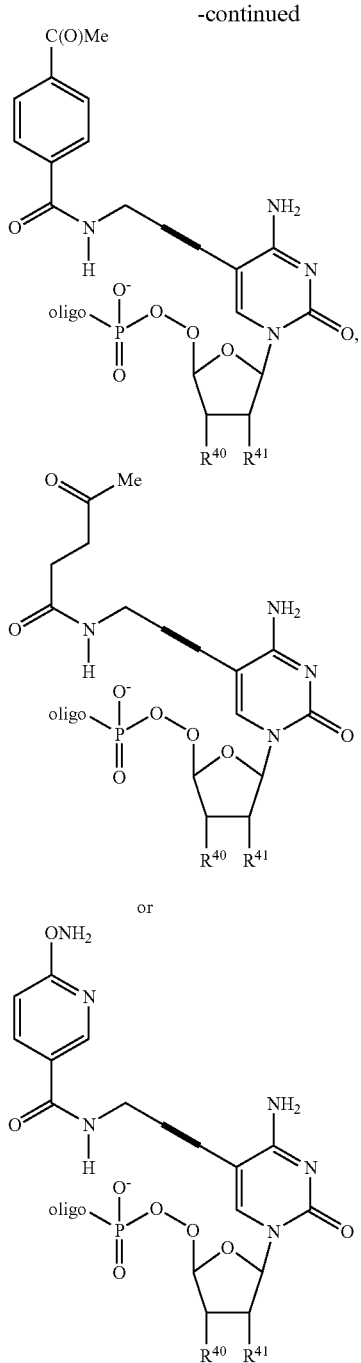

wherein $R^{40}$ is selected from the group consisting of an oligonucleotide, H and OH; and $R^{41}$ is selected from the group consisting of H and OH.

3. The compound of claim 1 that is immobilized on a surface.

4. The compound of claim 1 that is conjugated to a second component.

5. A method for immobilizing oligonucleotides on a solid surface, comprising the step of:
   reacting a compound of claim 1 or a plurality of said compounds with a solid surface; wherein:
   if the compound has a hydrazino or oxyamino group, the solid surface has a carbonyl group; or
   if the compound has a carbonyl group, the solid surface has a hydrazino or oxyamino group.

6. An immobilized oligonucleotide prepared by the method of claim 5.

7. A method for formation of an oligonucleotide conjugate, comprising the step of:
   reacting the compound of claim 1 with a second component to form an oligonucleotide conjugate;
   wherein the compound and the second component comprise complementary groups.

8. An oligonucleotide conjugate prepared by the method of claim 7.

9. The conjugate of claim 4, wherein the second component is selected from the group consisting of a fluorescein, a rhodamine and a cyanine dye.

10. A method of preparation of a hydrazino, oxyamino or carbonyl modified nucleoside triphosphate, comprising the steps of: (i) derivatizing a carboxylic acid selected from an ω-carbonyl, an ω-protected hydrazino, and an ω-protected oxyamino substituted carboxylic acid as the corresponding active ester;

(ii) reacting the resulting active ester with an amino substituted nucleoside triphosphate; and (iii) deprotecting the hydrazino or oxyamino group, if present.

* * * * *